(12) United States Patent
Reed et al.

(10) Patent No.: US 7,491,700 B2
(45) Date of Patent: Feb. 17, 2009

(54) CONVERSION OF APOPTOTIC PROTEINS

(75) Inventors: John C. Reed, Rancho Santa Fe, CA (US); Xiao-kun Zhang, San Diego, CA (US); Bin Guo, Fargo, ND (US); Bingzhen Lin, La Jolla, CA (US); Siva Kumar Kolluri, San Diego, CA (US)

(73) Assignee: The Burnham Institute, La Jolla, CA (US)

( * ) Notice: Subject to any disclaimer, the term of this patent is extended or adjusted under 35 U.S.C. 154(b) by 16 days.

(21) Appl. No.: 11/619,965

(22) Filed: Jan. 4, 2007

(65) Prior Publication Data
US 2007/0117753 A1 May 24, 2007

Related U.S. Application Data

(60) Division of application No. 11/245,845, filed on Oct. 7, 2005, now Pat. No. 7,176,277, which is a continuation of application No. 10/735,418, filed on Dec. 11, 2003, now Pat. No. 6,994,979.

(60) Provisional application No. 60/433,535, filed on Dec. 12, 2002.

(51) Int. Cl.
*G01N 33/53* (2006.01)
*A61K 38/00* (2006.01)
*C07K 1/00* (2006.01)
*C07K 16/00* (2006.01)
*C07H 21/02* (2006.01)
*C07H 21/00* (2006.01)

(52) U.S. Cl. .................. 514/12; 530/300; 530/350; 530/388.8; 530/7.1; 530/375; 536/23.1; 536/23.5

(58) Field of Classification Search ............... None
See application file for complete search history.

(56) References Cited

U.S. PATENT DOCUMENTS

| | | | |
|---|---|---|---|
| 6,498,195 | B2 | 12/2002 | Rosen et al. |
| 6,994,976 | B1 | 2/2006 | Tittle et al. |
| 2002/0137667 | A1 | 9/2002 | Chuenkova et al. |

OTHER PUBLICATIONS

Zhang, X. Novel Molecular Target for Breast Cancer Prevention and Treatment. Annual rept. Jun. 1, 2001-May 31, 2002, pp. 1-15.*
Zhang, X. Orphan Receptor TR3/nur77 and Apoptosis in Prostate Cancer Cells. Annual rept. Jul. 1, 2001-Jun. 30, 2002, pp. 1-11.*
Bohm et al., "The 5'-untranslated region of p23 mRNA form the Ehrlich ascites tumor is involved in translation control of the growth related protein p23" 1991, *Biomed Biochim Acta* 50:1193-203.
Buolamwini, "Novel anticancer drug discovery" 1999, *Curr Opin Chem Biol* 3:500-509.
Chang et al., "Isolation and characterization of human TR3 receptor: a member of steriod receptor superfamily" 1989, *Steroid Biochem* 34:391-395.
Cheng et al., "Functional redundancy of Nur77 and Nor-1 orphan steroid receptors in T-cell apoptosis" 1997, *EMBO J* 16:1865.
Cheng et al., "Conversion of Bcl-2 to a Bax-like Death Effector by Caspases" 1997, *Science* 278:1966-1968.
Degterev et al., "Identification of small-molecule inhibitors of interaction between the BH3 domain and Bcl-$X_L$" 2001, *Nat Cell Biol* 3:173-182.
Del Bello et al., "Cleavage of Bcl-2 in oxidant- and cisplatin-induced apoptosis of human melanoma cells" 2001, *Oncogene* 20:4591-4595.
Enyedy et al., "Discovery of Small-Molecule Inhibitors of Bcl-2 through Structure-Based Computer Screening" 2001, *J Med Chem* 44:4313-4324.
Fadeel et al., "Cleavage of Bcl-2 is an early event in chemotherapy-induced apoptosis of human myloid leukemia cells" 1999, *Leukemia* 13:719-728.
Finnegan et al., "Induction of apoptosis in prostate carcinoma cells by BH3 peptides which inhibit Bak/Bcl-2 interactions" 2001, *Br J Cancer* 85:115-121.
Fujita et al., "Involvement of Bcl-2 Cleavage in the Acceleration of VP-16-Induced U937 Cell Apoptosis" 1998, *Biochem Biophys Res Commun* 246:484-488.
Grandgirard et al., "Alphaviruses induce apoptosis in Bcl-2 overexpressing cells; evidence for a caspase-mediated, proteolytic inactivation of Bcl-2" 1998, *EMBO J* 17:1268-1278.
Lewis et al., "Inhibition of virus-induced neuronal apoptosis by Bax" 1999, *Nat Med* 5:832-835.
Li et al., "Molecular Determinants of AHPN (CD437)-Induced Growth Arrest and Apoptosis in Human Lung Cancer Cell Lines" 1998, *Mol Cell Biol* 18:4719.
Li et al., "Cytochrome c Release and Apoptosis Induced by Mitochondrial Targeting of Nuclear Orphan Receptor TR3" 2000, *Science* 289:1159.
Li et al. "Characterization of Fortillin, a novel antiapoptotic protein" 2001, *JBC* 276:47542-47549.
Liu et al., "Apoptotic signals delivered through the T-cell receptor of a T-cell hybrid require the Immediate-early gene nur77" 1994, *Nature* 367:281.
Petros et al. "Rational for Bcl-XL/Bad peptide complex formation from structure, mutagenesis and biophysical studies" 2000, *Protein Science* 9:2528-2534.
Reed, John C. "Bcl-2 Family Proteins: Regulators of Apoptosis and Chemoresistance in Hematologic Maliganancis" 1997 *Sem Hematol* 34:9-19.
Tzung et al., "Antimycin A mimics a cell-death-inducing Bcl-2 homology domain 3" 2001, *Nat Cell Biol* 3:183-191.
Uemura et al., "Antisense TR3 Orphan Receptor Can Increase Prostate Cancer Cell Viability with Etoposide Treatment" 1998, *Endocrinology* 129:2329.
Weih et al., "Apoptosis of nur77/N10-Transgenic Thymocytes Involves the Fas/Fas Ligand Pathway" 1996, *PNAS USA* 93:5533.
Woronicz et al., "Requirement for the Orphan steroid receptor Nur77 in apoptosis of T-cell hybridomas" 1994, *Nature* 367:277.
Young et al., "Tumor-Promoting Phorbol Ester-Induced Cell Death and Gene Expression in a Human Prostate Denocarcinoma Cell Line" 1994, *Oncol.Res.* 6:203.

* cited by examiner

*Primary Examiner*—Rebecca E. Prouty
*Assistant Examiner*—Iqbal H Chowdhury
(74) *Attorney, Agent, or Firm*—Knobbe Martens Olson & Bear LLP

(57) ABSTRACT

Compounds that modulate the function of anti-apoptotic proteins such as Bcl-2 and Bcl-$X_L$ are identified. These compounds have the ability to convert the activity of Bcl-2-family member proteins from anti-apoptotic to pro-apoptotic. Methods for inducing apoptosis are described, together with methods for identifying molecules that induce apoptosis through interaction with Bcl-2-family members.

5 Claims, 9 Drawing Sheets

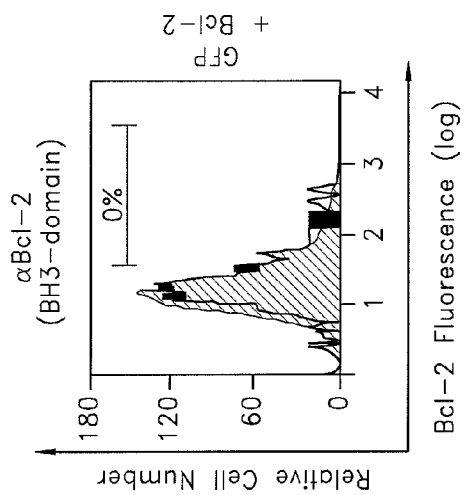
FIG. 9A
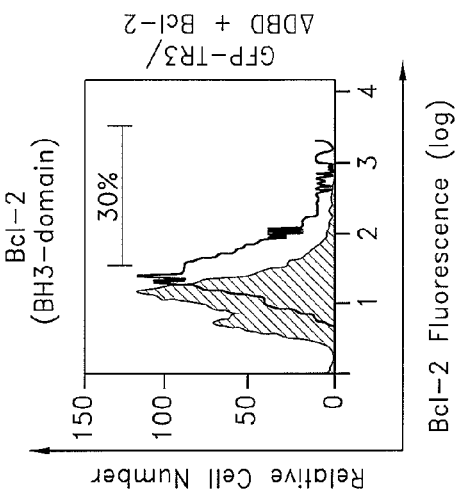
FIG. 9B
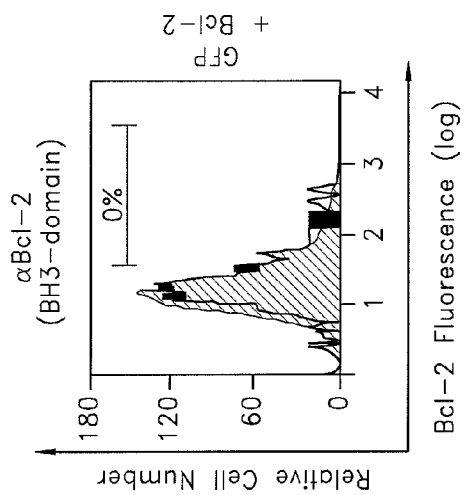
FIG. 9C
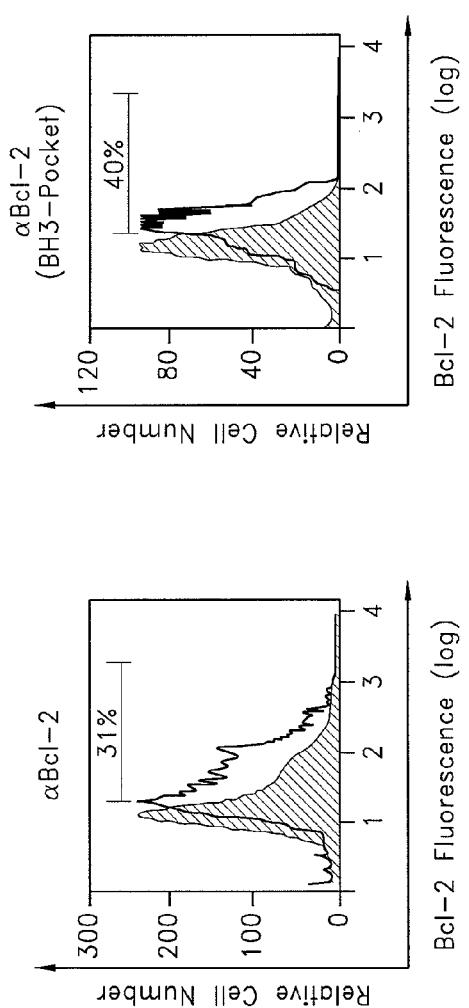
FIG. 9D
FIG. 9E
FIG. 9F

CONVERSION OF APOPTOTIC PROTEINS

RELATED APPLICATIONS

This application is a divisional of U.S. application Ser. No. 11/245,845, filed Oct. 7, 2005, now U.S. Pat. No. 7,176,277, which is a continuation of U.S. application Ser. No. 10/735,418, filed Dec. 11, 2003, now U.S. Pat. No. 6,994,979, which claims priority of U.S. Provisional Application 60/433,535, filed Dec. 12, 2002, all of which are herein incorporated by reference in their entireties.

This invention was made in part with United States government support under grant numbers NIH CA60988, CA8700, and GM60554 awarded by the National Institutes of Health, and USARMY PCRP-001590 and BC-001182 awarded by the Department of Defense. The U.S. government has certain rights in this invention.

BACKGROUND OF THE INVENTION

1. Field of the Invention

Compounds are provided herein that bind to Bcl-2-family member peptides and alter their apoptosis regulatory function. More specifically, the use of peptides expressed by the TR3 gene or chemical compounds that mimic the effects of TR3 to induce Bcl-2 or Bcl-$X_L$ to have a pro-apoptotic effect and to induce a conformational change, and the use of the protein TCTP or chemical compounds that mimic the effects of TCTP to induce Bcl-$X_L$ to have a pro-apoptotic effect, are described.

2. Description of the Related Art

Apoptosis, also known as programmed cell death, is a physiological process through which the body disposes of unneeded or undesirable native cells. The process of apoptosis is used during development to remove cells from areas where they are no longer required, such as the interior of blood vessels or the space between digits. Apoptosis is also important in the body's response to disease. Cells that are infected with some viruses can be stimulated to undergo apoptosis, thus preventing further replication of the virus in the host organism.

Impaired apoptosis due to blockade of the cell death-signaling pathways is involved in tumor initiation and progression, since apoptosis normally eliminates cells with increased malignant potential such as those with damaged DNA or aberrant cell cycling (White 1996 *Genes Dev* 10:1-15). The majority of solid tumors are protected by at least one of the two cell death antagonists, Bcl-2 or Bcl-$X_L$. Members of the Bcl-2-family are known to modulate apoptosis in different cell types in response to various stimuli. Some members of the family act to inhibit apoptosis, such as Bcl-2 and Bcl-$X_L$, while others, such as BAX, BAK, Bid, and Bad, promote apoptosis. The ratio at which these proteins are expressed can decide whether a cell undergoes apoptosis or not. For instance, if the Bcl-2 level is higher than the BAX level, apoptosis is suppressed. If the opposite is true, apoptosis is promoted. Bcl-2 overexpression contributes to cancer cell progression by preventing normal cell turnover caused by physiological cell death mechanisms, and has been observed in a majority of cancers (Reed 1997 *Sem Hematol* 34:9-19; Buolamwini 1999 *Curr Opin Chem Biol* 3:500-509). The expression levels of Bcl-2 proteins often correlate with resistance to a wide spectrum of chemotherapeutic drugs and γ-radiation therapy. Paradoxically, high levels of Bcl-2 also associate with favorable clinical outcomes for patients with some types of cancers. Therefore, Bcl-2 represents an excellent target for the treatment of cancer, especially those in which Bcl-2 is overexpressed and for which traditional therapy has failed.

Biological approaches targeted at Bcl-2 using antisense oligonucleotides have been shown to enhance tumor cell chemosensitivity. Bcl-2 antisense oligonucleotides in combination with chemotherapy are currently in phase II/III clinical trials for the treatment of patients with lymphoma and malignant melanoma, and further trials with patients with lung, prostate, renal, or breast carcinoma are ongoing or planned (Reed 1997 supra; Piche et al. 1998 *Cancer Res* 58:2134-2140; Webb et al. 1997 *Lancet* 349:1137-1141; Jansen et al. 1998 *Nat Med* 4:232-234; Waters et al. 2000 *J Clin Oncol* 18:1812-1823). Recently, cell-permeable Bcl-2 binding peptides and chemical inhibitors that target Bcl-2 have been developed, and some of them have been shown to induce apoptosis in vitro and in vivo (Finnegan et al. 2001 *Br J Cancer* 85:115-121; Enyedy et al. 2001 *J Med Chem* 44:4313-4324; Tzung et al. 2001 *Nat Cell Biol* 3:183-191; Degterev et al. 2001 *Nat Cell Biol* 3:173-182).

One well-established apoptotic pathway involves mitochondria (Green and Reed, 1998 *Science* 281:1309-1312; Green and Kroemer, 1998 *Trends Cell Biol* 8:267-271). Cytochrome c is exclusively present in mitochondria and is released from mitochondria in response to a variety of apoptotic stimuli. Many Bcl-2-family proteins reside on the mitochondrial outer membrane. Bcl-2 prevents mitochondrial disruption and the release of cytochrome c from mitochondria, while BAX and BAK create pores in mitochondrial membranes and induce cytochrome c release. Recent evidence has indicated, however, that Bcl-2 under certain conditions can function as a pro-apoptotic molecule (Finnegan et al. 2001, supra; Fujita et al. 1998 *Biochem Biophys Res Commun* 246:484-488; Fadeel et al. 1999 *Leukemia* 13:719-728; Grandgirard et al. 1998 *EMBO J.* 17:1268-1278; Cheng et al. 1997 *Science* 278:1966-1968; Del Bello et al. 2001 *Oncogene* 20:4591-4595). Bcl-2 can be cleaved by caspase-3 and thus be converted to a pro-apoptotic protein similar to BAX (Cheng et al. 1997, supra). Conversely, BAX has also been shown to inhibit neuronal cell death when infected with Sinbis virus (Lewis et al. 1999 *Nat Med* 5:832-835). These observations suggest that members of the Bcl-2-family have reversible roles in the regulation of apoptosis and have the potential to function either as a pro-apoptotic or anti-apoptotic molecule.

Members of the Bcl-2-family of proteins are highly related in one or more specific regions, commonly referred to as Bcl-2 homology (BH) domains. BH domains contribute at multiple levels to the function of these proteins in cell death and survival. The BH3 domain, an amphipathic α-helical domain, was first delineated as a stretch of 16 amino acids in Bak that is required for this protein to heterodimerize with anti-apoptotic members of the Bcl-2-family and to promote cell death. All proteins in the Bcl-2-family contain a BH3 domain, and this domain can have a death-promoting activity that is functionally important. The BH3 domain acts as a potent "death domain" and there is a family of pro-apoptotic proteins that contain BH3 domains which dimerize via those BH3 domains with Bcl-2, Bcl-$X_L$ and other anti-apoptotic members of the Bcl-2 family. Structural studies revealed the presence of a hydrophobic pocket on the surface of Bcl-$X_L$ and Bcl-2 that binds the BH3 peptide. Interestingly, the anti-apoptotic proteins Bcl-$X_L$ and Bcl-2 also possess BH3 domains, but in these anti-apoptotic proteins, the BH3 domain is buried in the core of the protein and not exposed for dimerization. (Kelekar and Thompson 1998 *Trends Cell Biol* 8:324). NMR structural analysis of the Bcl-$X_L$/Bak BH3 peptide complex showed that the Bak BH3 domain binds to the hydrophobic cleft formed in part by the BH1, BH2 and BH3 domains of Bcl-$X_L$ (Sattler 1997 *Science* 275:983; Degterev 2001 *Nature Cell Biol* 3:173-182). BH3-domain-mediated homodimerizations and heterodimerizations have a key role in regulating apoptotic functions of the Bcl-2-family (Diaz et al. 1997 *J Biol Chem* 272:11350; Degterev 2001 *Nature Cell Biol* 3:173-182).

The orphan receptor TR3 (also known as nur77 or nerve growth factor-induced clone B NGFI-B) (Chang and Kokontis 1988 *Biochem Biophys Res Commun* 155:971; Hazel et al. 1988 *PNAS USA* 85:8444) functions as a nuclear transcription factor in the regulation of target gene expression (Zhang and Pfahl 1993 *Trends Endocrinol Metab* 4:156-162; Tsai and O'Malley 1994 *Annu Rev Biochem* 63:451; Kastner et al. 1995 *Cell* 83:859; Mageldorf and Evens 1995 *Cell* 83:841). TR3 was originally isolated as an immediate-early gene rapidly expressed in response to serum or phorbol ester stimulation of quiescent fibroblasts (Hazel et al., supra; Ryseck, et al. 1989 *EMBO J.* 8:3327; Nakai et al. 1990 *Mol Endocrinol* 4:1438; Herschman 1991 *Annul Rev Biochem* 60:281). Other diverse signals, such as membrane depolarization and nerve growth factor, also increase TR3 expression (Yoon and Lau 1993 *J Biol Chem* 268:9148). TR3 is also involved in the regulation of apoptosis in different cell types (Woronicz et al. 1994 *Nature* 367:277; Liu et al. 1994 *Nature* 367:281; Weih et al. PNAS USA 93:5533; Chang et al. 1997 *EMBO J.* 16:1865; Li et al. 1998 *Mol Cell Biol* 18:4719; Uemura and Chang, 1998 *Endocrinology* 129:2329; Young et al. 1994 *Oncol Res* 6:203). It is rapidly induced during apoptosis of immature thymocytes and T-cell hybridomas (Woronicz et al., supra; Liu et al., supra), in lung cancer cells treated with the synthetic retinoid 6-[3-(1-adamantyl)-4-hydroxyphenyl]-2-naphthalene carboxylic acid (AHPN) (Li et al., supra) (also called CD437), and in prostate cancer cells treated with different apoptosis inducers (Uemura and Chang, supra; Young et al., supra). Inhibition of TR3 activity by overexpression of dominant-negative TR3 or its antisense RNA inhibits apoptosis, whereas constitutive expression of TR3 results in massive apoptosis (Weih et al., supra; Cheng et al., supra).

Further studies of TR3 have yielded a better understanding of its mechanism of action in apoptosis (Li et al. 2000 *Science* 289:1159). First, several apoptosis inducing agents which also induced TR3 expression in human prostate cancer cells were identified. These included the AHPN analog 6-[3-(1-adamantyl)-4-hydroxyphenyl]-3-chloro-2-naphthalenecarboxylic acid (MM11453), the retinoid (Z)-4-[2-bromo-3-(5,6,7,8-tetrahydro-3,5,5,8,8-pentamethyl-2-naphthalenyl)propenoyl]benzoic acid (MM11384), the phorbol ester 12-O-tetradecanoyl phorbol-13-acetate (TPA), the calcium ionophore A23187, and the etoposide VP-16. Second, it was found that the transactivation activity of TR3 is not required for its role in inducing apoptosis, as demonstrated by an experiment that showed that apoptosis inducing agents blocked the expression of a TR3 target reporter gene. This was further supported by the finding that a TR3 mutant deprived of its DNA binding domain (DBD) was still competent for inducing apoptosis. Third, TR3 was found to relocalize to the outer surface of the mitochondria in response to some apoptotic stimuli. TR3, visualized in vivo by tagging with Green Fluorescent Protein (GFP), was shown to relocalize from the nucleus to the mitochondria in response to apoptosis-inducing agents. Fractionation studies showed that TR3 was associating with the mitochondria-enriched heavy membrane fraction, and proteolysis accessibility studies on purified mitochondria confirmed that TR3 was associating with the outer surface of the mitochondria, where Bcl-2-family members are also found. Fourth, TR3 was shown to be involved in the regulation of cytochrome c release from the mitochondria. Inhibition of TR3 activity by expression of TR3 antisense RNA blocked the release of cytochrome c and mitochondrial membrane depolarization in cells stimulated with TPA and MM11453. Furthermore, incubating purified mitochondria with recombinant TR3 protein resulted in cytochrome c release.

Li et al., 2000, supra, further explored the function of TR3 through mutation of the protein. A TR3 mutant which had the DNA binding domain (amino acid residues168-467) removed (TR3/ΔDBD) no longer localized in the nucleus in non-stimulated cells, but instead was consistently found in mitochondria. This localization phenotype was accompanied by a constant release of cytochrome c from the mitochondria. Three other deletion mutants were also generated and assayed: an amino-terminal deletion of 152 amino acids referred to as TR3/Δ1, a 26 amino acid carboxy-terminal deletion referred to as TR3/Δ2, and a 120 amino acid carboxy-terminal deletion referred to as TR3/Δ3. The TR3/Δ1 protein did not relocalize to the mitochondria in response to TPA, but maintained a nuclear localization. TR3/Δ1 had a dominant negative effect, preventing the relocalization of full-length TR3 to the mitochondria and inhibiting apoptosis. Mitochondrial targeting was still observed in TR3/Δ2 protein expressing cells, but not in TR3/Δ3 protein cells in response to TPA treatment. These results indicated that carboxy-terminal and amino-terminal sequences are crucial for mitochondrial targeting of TR3 and its regulation.

Experiments designed to alter the localization of TR3/ΔDBD by fusing it to various cellular localization signals showed that TR3 must have access to the mitochondria in order to induce its pro-apoptotic effect. When TR3/ΔDBD was fused to a nuclear localization sequence, a plasma membrane targeting sequence, or an ER-targeting sequence, TR3/ΔDBD was not targeted to the mitochondria and no induction of cytochrome c release was observed.

The translationally controlled tumor-associated protein (TCTP) is conserved across a wide range of eukaryotes and shows no significant sequence homology with any other proteins. The precise function of the family remains elusive. TCTP has been described as growth related protein. TCTP was originally identified as a serum-inducible 23-kDa protein band that undergoes an early and prominent increase upon serum stimulation in tissue culture cells (Benndorf et al. 1988 *Exp Cell Res* 174:130). TCTP mRNA is expressed at constant levels in both growing and nongrowing cells, and the translation is regulated by its polypyrimidine-rich 5' untranslated region (Bohm et al. 1991 *Biomed Biochim Acta* 50:1193; 174:130). TCTP was shown to be one of the first proteins to be induced in Ehrlich ascites tumor cells following mitotic stimulation (Bohm et al. 1989 *Biochem Int* 19:277) and has been found to be amongst a small group of *Schizosaccharomyces pombe* proteins that are repressed in response to conditions that arrest cell growth, such as ammonium starvation (Bonnet C. et al 2000 *Yeast* 16:23). TCTP was recently shown to be a tubulin-binding protein that dynamically interacts with microtubules during the cell cycle. In addition, TCTP levels in overexpressing cells were correlated with microtubule stabilization and reduced growth rate in vivo (Gachet et al. 1999 *J Cell Sci* 112:1257). The expression of TCTP also appears to be regulated at two distinct levels in response to the concentration of calcium in different cellular compartments. Whereas depletion of the ER store causes an increase in TCTP mRNA abundance, increased cytosolic calcium concentrations regulate gene expression at the post-transcriptional level (Xu et al. 1999 *Biochem J* 342:683). The solution structure of TCTP forms a structural superfamily with the Mss4/Dss4 family of proteins, which bind to the GDP/GTP-free form of Rab proteins (members of the Ras superfamily) and have been termed guanine nucleotide-free chaperones (Thaw et al. 2001 *Nat Struct Biol* 8:701).

The identification of compounds having the ability to alter the activity of Bcl-2-family members from anti-apoptotic to pro-apoptotic would have important therapeutic applications, for example, in the treatment of cancer and other diseases.

SUMMARY OF THE INVENTION

One aspect of the invention pertains to the discovery of molecules that modulate the activity of Bcl-2-family members in their regulation of apoptosis. More specifically, it concerns regulators of apoptosis which inhibit proteins such as Bcl-2 and Bcl-$X_L$ and can induce a conformational change in these proteins resulting in pro-apoptotic properties.

The scope of the compositions and methods described herein includes the use of proteins and their respective genes, peptides, peptide analogs, antibodies, polynucleotides and small molecules to regulate the apoptotic effect of Bcl-2-family members.

In one embodiment, a compound which binds to Bcl-2 and modulates the activity of Bcl-2 in a cell so as to be inductive of apoptosis, without cleaving Bcl-2, is described. The compound can be a peptide, a peptidomimetic, an antibody or a small organic molecule. In one embodiment, the compound comprises TR3, whereas in another embodiment, the compound comprises the DC1 region of TR3. In a further embodiment, the compound comprises an antibody which mimics the action of TR3 on Bcl-2.

In another embodiment, a compound which binds to Bcl-$X_L$ and modulates the activity of Bcl-$X_L$ in a cell so as to be inductive of apoptosis, without cleaving Bcl-$X_L$, is disclosed. The compound can be a peptide, peptidomimetic, or a small organic molecule. In one embodiment, the compound comprises TCTP, whereas in another embodiment, the compound comprises a peptidomimetic which mimics TCTP.

Yet another embodiment of the invention is a method of inducing apoptosis in a mammalian cell, comprising contacting the cell with an effective amount of a compound which binds to Bcl-2 and modulates the activity of Bcl-2 so as to be inductive of apoptosis. Similarly, another embodiment includes a method of inducing apoptosis in a mammalian cell, comprising contacting the cell with an effective amount of a compound which binds to Bcl-$X_L$ and modulates the activity of Bcl-$X_L$ in the cell so as to be inductive of apoptosis.

Another embodiment of the invention includes a method of inhibiting apoptosis in a mammalian cell, comprising contacting the cell with an effective amount of a compound that prevents the binding of TR3 and Bcl-2. Another embodiment includes a method of inhibiting apoptosis in a mammalian cell, comprising contacting the cell with an effective amount of a compound that prevents the binding of TCTP and Bcl-$X_L$. Another embodiment includes a method of identifying molecules that inhibit apoptosis by preventing binding of TR3 to Bcl-2 or binding of TCTP to Bcl-$X_L$.

Still another embodiment of the invention includes a method of identifying molecules that induce apoptosis, comprising determining the ability of said molecule to bind to a Bcl-2-family protein and modulate the activity of said protein so as to be inductive of apoptosis.

BRIEF DESCRIPTION OF THE DRAWINGS

FIGS. 9 *a-f* is a series of graphs that illustrate the Bcl-2 domain which undergoes a conformational change when TR3 binds.

DETAILED DESCRIPTION OF THE PREFERRED EMBODIMENT

I. Definitions and General Parameters

Figure 1:
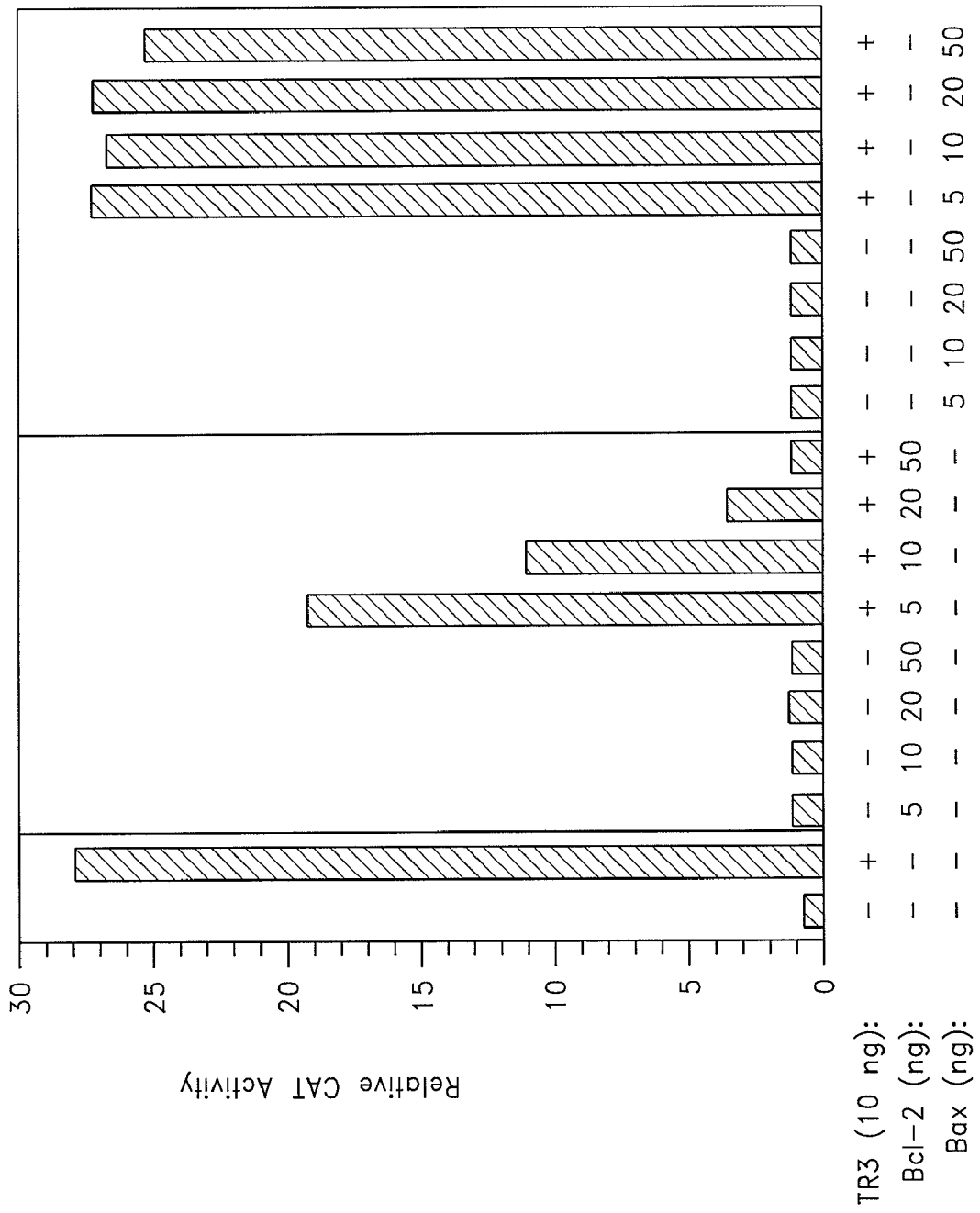
FIG. 1 shows the results of a reporter gene assay in CV-1 cells, which demonstrates the inhibition of TR3-dependent transactivation by Bcl-2.
Figure 2:
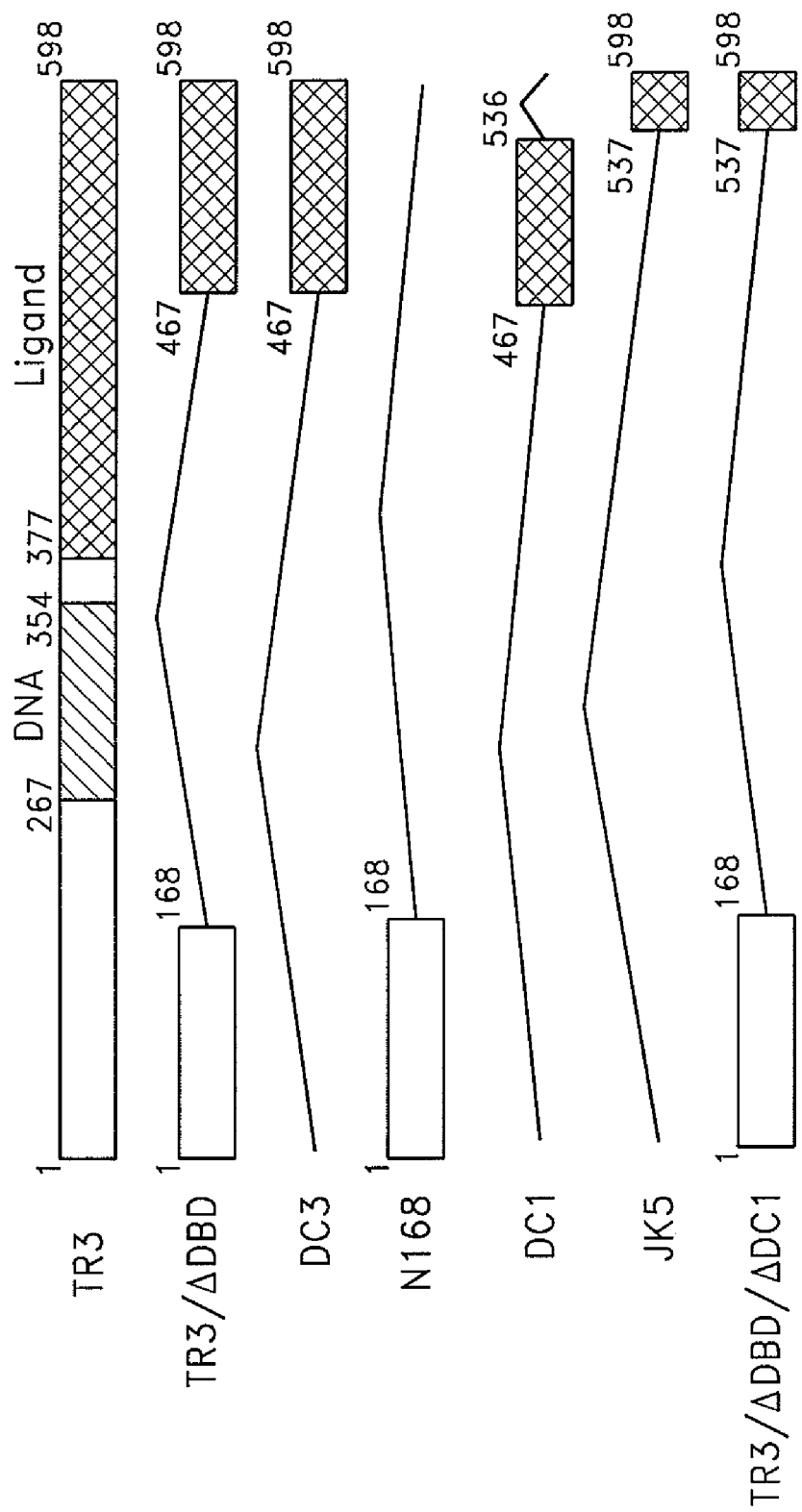
FIG. 2 is a schematic representation of TR3 mutants, indicating the DNA-binding and ligand-binding domains of TR3.

The following definitions are set forth to illustrate and define the meaning and scope of the various terms used to describe the invention herein.

As used herein, "pharmaceutically or therapeutically acceptable carrier" refers to a carrier medium which does not interfere with the effectiveness of the biological activity of the active ingredients and which is not toxic to the host or patient.

As used herein, "stereoisomer" refers to a chemical compound having the same molecular weight, chemical composition, and constitution as another, but with the atoms grouped differently. That is, certain identical chemical moieties are at different orientations in space and, therefore, when pure, have the ability to rotate the plane of polarized light. However, some pure stereoisomers may have an optical rotation that is so slight that it is undetectable with present instrumentation. The compounds described herein may have one or more asymmetrical carbon atoms and therefore include various stereoisomers. All stereoisomers are included within the scope of the present invention.

As used herein, "therapeutically- or pharmaceutically-effective amount" as applied to the disclosed compositions refers to the amount of composition sufficient to induce a desired biological result. That result can be alleviation of the signs, symptoms, or causes of a disease, or any other desired alteration of a biological system. For example, the result can involve a decrease and/or reversal of cancerous cell growth.

As used herein, "homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. An "unrelated" or "non-homologous" sequence shares less than about 40% identity, though preferably less than about 25% identity, with one of the sequences described herein.

In addition to peptides consisting only of naturally-occurring amino acids, peptidomimetics or peptide analogs are also considered. Peptide analogs are commonly used in the pharmaceutical industry as non-peptide drugs with properties analogous to those of the template peptide. These types of non-peptide compounds are termed "peptide mimetics" or "peptidomimetics" (see, e.g., Luthman et al. 1996 *A Textbook of Drug Design and Development*, 14:386-406, 2nd Ed., Harwood Academic Publishers; Grante, 1994 *Angew Chem Int Ed Engl* 33:1699-1720; Fauchere 1986 *Adv Drug Res* 15:29; Evans et al. 1987 *J Med Chem* 30:229, all of which are incorporated by reference). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as naturally-occurring receptor-binding polypeptide, but have one or more peptide linkages optionally replaced by a linkage selected from the group consisting of: —CH$_2$NH—, —CH$_2$S—, —CH$_2$—CH$_2$—, —CH=CH— (cis and trans), —COCH$_2$—, —CH(OH)CH$_2$—, and —CH$_2$SO—, by methods known in the art and further described in the following references: Spatola, 1983 In: *Chemistry and Biochemistry of Amino Acids, Peptides, and Proteins*, B. Weinstein, eds., Marcel Dekker, New York, p. 267; Hudson et al. 1979 *Int J Pept Prot Res* 14:177-185 (1979) (—CH$_2$NH—, CH$_2$CH$_2$—); Spatola et al. 1986 *Life Sci* 38:1243-1249 (—CH$_2$—S); Hann 1982 *J Chem Soc Perkins Trans I* 307-314 (—CH—CH—, cis and trans); Almquist et al. 1980 *J Med Chem* 23:1392-1398 (—COCH$_2$—); Jennings-White et al. 1982 *Tetrahedron Lett* 23:2533 (—COCH$_2$—); Szelke et al. European Appln. EP 45665 (1982) (—CH(OH)CH$_2$—); Holladay et al. 1983, *Tetrahedron Lett* 24:4401-4404 (—C(OH)CH$_2$—); and Hruby 1982 *Life Sci* 31:189-199 (—CH$_2$—S—); each of which is incorporated herein by reference. A particularly preferred non-peptide linkage is —CH$_2$NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) (e.g., immunoglobulin superfamily molecules) to which the peptidomimetic binds to produce the therapeutic effect. Derivatization (e.g., labeling) of peptidomimetics should not substantially interfere with the desired biological or pharmacological activity of the peptidomimetic. Generally, peptidomimetics of receptor-binding peptides bind to the receptor with high affinity and possess detectable biological activity (i.e., are agonistic or antagonistic to one or more receptor-mediated phenotypic changes).

Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo et al. 1992 *Annu Rev Biochem* 61:387), incorporated herein by reference); for example, by adding internal cysteine residues capable of forming intramolecular disulfide bridges which cyclize the peptide.

Synthetic or non-naturally occurring amino acids refer to amino acids which do not naturally occur in vivo but which, nevertheless, can be incorporated into the peptide structures described herein. Preferred synthetic amino acids are the D-α-amino acids of naturally occurring L-α-amino acid as well as non-naturally occurring D- and L-α-amino acids represented by the formula H$_2$NCHR$^5$COOH where R$^5$ is 1) a lower alkyl group, 2) a cycloalkyl group of from 3 to 7 carbon atoms, 3) a heterocycle of from 3 to 7 carbon atoms and 1 to 2 heteroatoms selected from the group consisting of oxygen, sulfur, and nitrogen, 4) an aromatic residue of from 6 to 10 carbon atoms optionally having from 1 to 3 substituents on the aromatic nucleus selected from the group consisting of hydroxyl, lower alkoxy, amino, and carboxyl, 5)-alkylene-γ where alkylene is an alkylene group of from 1 to 7 carbon atoms and Y is selected from the group consisting of (a) hydroxy, (b) amino, (c) cycloalkyl and cycloalkenyl of from 3 to 7 carbon atoms, (d) aryl of from 6 to 10 carbon atoms optionally having from 1 to 3 substituents on the aromatic nucleus selected from the group consisting of hydroxyl, lower alkoxy, amino and carboxyl, (e) heterocyclic of from 3 to 7 carbon atoms and 1 to 2 heteroatoms selected from the group consisting of oxygen, sulfur, and nitrogen, (f) —C(O)R$^2$ where R$^2$ is selected from the group consisting of hydrogen, hydroxy, lower alkyl, lower alkoxy, and —NR$^3$R$^4$ where R$^3$ and R$^4$ are independently selected from the group consisting of hydrogen and lower alkyl, (g) —S(O)$_n$R$^6$ where n is an integer from 1 to 2 and R$^6$ is lower alkyl and with the proviso that R$^5$ does not define a side chain of a naturally occurring amino acid.

Other preferred synthetic amino acids include amino acids wherein the amino group is separated from the carboxyl group by more than one carbon atom such as beta (β)-alanine, gamma (γ)-aminobutyric acid, and the like.

Particularly preferred synthetic amino acids include, by way of example, the D-amino acids of naturally occurring L-amino acids, L-(1-naphthyl)-alanine, L-(2-naphthyl)-alanine, L-cyclohexylalanine, L-2-aminoisobutyric acid, the sulfoxide and sulfone derivatives of methionine (i.e., HOOC—(H$_2$NCH)CH$_2$CH$_2$—S(O)$_n$R$^6$) where n and R$^6$ are as defined above as well as the lower alkoxy derivative of methionine (i.e., HOOC—(H$_2$NCH)CH$_2$CH$_2$—OR$^6$ where R$^6$ is as defined above).

II. Overview

Compounds that bind to Bcl-2-family members and alter their function in apoptosis are also provided. These compounds include "lead" peptide compounds and "derivative" compounds constructed so as to have the same or similar molecular structure or shape as the lead compounds but that differ from the lead compounds either with respect to susceptibility to hydrolysis or proteolysis and/or with respect to other biological properties, such as increased affinity for the receptor.

The examples described herein demonstrate that the nuclear-to-mitochondrial pathway of TR3 can be extended to lung and breast cancer cells. In addition, it is shown that Bcl-2 acts as a mitochondrial receptor of TR3 through their physical interaction. In response to various apoptotic stimuli, the expression of the TR3 protein is increased and its localization is altered from nuclear to cytoplasmic, more specifically to the outer member of mitochondria. This association with the mitochondria is the result of binding to the Bcl-2, whose normal function is the inhibition of apoptosis, particularly the inhibition of the release of cytochrome c from the mitochondria. High expression of TR3/ΔDBD (a form of TR3 without its DNA-binding domain) induces cytochrome c release and apoptosis only in cells expressing Bcl-2, indicating that TR3 modulates the function of Bcl-2 from anti-apoptotic to pro-apoptotic, without cleaving the Bcl-2 protein. Further data show that TR3 induces a conformational change in Bcl-2 which may cause the function of Bcl-2 to be modified from an anti-apoptotic to a pro-apoptotic protein. Mutational analysis indicated that the C-terminal domain of TR3, which contains several α-helices, is responsible for interacting with Bcl-2. A small fragment with only 69 amino acids (DC1) is sufficient for interacting with Bcl-2 and inducing apoptotic potential of Bcl-2. When analyzing the Bcl-2 domains involved in the interaction, it was observed that mutations in the hydrophobic pocket of Bcl-2 did not affect its interaction with TR3. Moreover, the N-terminal domain of Bcl-2, containing the loop region and BH4 domain, was able to interact with TR3/ΔDBD. Deletion of BH4 domain from Bcl-2 did not affect the interaction of TR3/ΔDBD with Bcl-2, implying that the loop region of Bcl-2 was responsible for interaction. In addition, DC1 and BH3-only Bcl-Gs did not compete for binding to Bcl-2. Instead, Bcl-Gs enhanced the binding of DC1 to Bcl-2. Thus, Bcl-2 was found to interact with TR3 in a manner that is different from its interaction with Bcl-2-family proteins containing only the BH3 domain.

Specific interaction of TR3 with Bcl-2 is essential for TR3 to target mitochondria and results in conversion of Bcl-2 from an anti-apoptotic to a pro-apoptotic molecule. Concomitantly, the conformation of Bcl-2 is changed by TR3 resulting in the exposure of the otherwise hidden BH3 domain. Peptides derived from the specific Bcl-2-interacting domain of TR3, such as DC1, will mimic its effect, as will peptide analogs and small molecules designed to mimic the binding properties of the peptides. Further, antibodies may be identified which also mimic the effect of TR3. Peptides, antibodies, analogs, and small molecules that specifically interact with Bcl-2 will effectively induce apoptosis of cancer cells, thus restricting tumor growth. In addition, the results provide a molecular basis for developing various agents for treating cancers and other therapeutic applications.

Similarly, TCTP was identified as another apoptosis regulatory molecule which binds to an anti-apoptotic Bcl-2 related protein. While overexpression of TCTP in cells induces apoptosis, this induction is even more pronounced when the Bcl-$X_L$ is co-expressed with it; like TR3, TCTP is converting an anti-apoptotic protein to a pro-apoptotic protein. Peptides, peptide analogs, and small molecules that mimic the binding of TCTP to Bcl-$X_L$ will also act to induce apoptosis.

III. Preparation of Peptides and Peptide Mimetics

A. Solid Phase Synthesis

The peptides disclosed herein can be prepared by classical methods known in the art, for example, by using standard solid phase techniques. The standard methods include exclusive solid phase synthesis, partial solid phase synthesis methods, fragment condensation, classical solution synthesis, and even recombinant DNA technology. See, e.g., Merrifield 1963 *J Am Chem Soc* 85:2149, incorporated herein by reference. On solid phase, the synthesis is typically commenced from the C-terminal end of the peptide using an alpha-amino protected resin. A suitable starting material can be prepared, for instance, by attaching the required alpha-amino acid to a chloromethylated resin, a hydroxymethyl resin, or a benzhydrylamine resin. One such chloromethylated resin is sold under the trade name BIO-BEADS SX-1™ by Bio Rad Laboratories (Richmond, Calif.) and the preparation of the hydroxymethyl resin is described by Bodonszky et al. 1966 *Chem Ind* (London), 38:1597. The benzhydrylamine (BHA) resin has been described by Pietta and Marshall, 1970, *Chem Comm* 650, and is commercially available from Beckman Instruments, Inc. (Palo Alto, Calif.) in the hydrochloride form.

Thus, the compounds disclosed herein can be prepared by coupling an alpha-amino protected amino acid to the chloromethylated resin with the aid of, for example, a cesium bicarbonate catalyst, according to the method described by Gisin, 1973 *Helv Chim Acta* 56:1467. After the initial coupling, the alpha-amino protecting group is removed by a choice of reagents including trifluoroacetic acid (TFA) or hydrochloric acid (HCl) solutions in organic solvents at room temperature.

The alpha-amino protecting groups are those known to be useful in the art of stepwise synthesis of peptides. Included are acyl type protecting groups (e.g., formyl, trifluoroacetyl, acetyl), aromatic urethane type protecting groups (e.g., benzyloxycarboyl (Cbz) and substituted Cbz), aliphatic urethane protecting groups (e.g., t-butyloxycarbonyl (Boc), isopropyloxycarbonyl, cyclohexyloxycarbonyl) and alkyl type protecting groups (e.g., benzyl, triphenylmethyl). Boc and Fmoc are preferred protecting groups. The side-chain protecting group remains intact during coupling and is not split off during the deprotection of the amino-terminus protecting group or during coupling. The side-chain protecting group must be removable upon the completion of the synthesis of the final peptide and under reaction conditions that will not alter the target peptide.

The side-chain protecting groups for Tyr include tetrahydropyranyl, tert-butyl, trityl, benzyl, Cbz, Z-Br-Cbz, and 2,5-dichlorobenzyl. The side-chain protecting groups for Asp include benzyl, 2,6-dichlorobenzyl, methyl, ethyl, and cyclohexyl. The side-chain protecting groups for Thr and Ser include acetyl, benzoyl, trityl, tetrahydropyranyl, benzyl, 2,6-dichlorobenzyl, and Cbz. The side-chain protecting group for Thr and Ser is benzyl. The side-chain protecting groups for Arg include nitro, Tosyl (Tos), Cbz, adamantyloxycarbonyl mesitoylsulfonyl (Mts), or Boc. The side-chain protecting groups for Lys include Cbz, 2-chlorobenzyloxycarbonyl (2Cl-Cbz), 2-bromobenzyloxycarbonyl (2-BrCbz), Tos, or Boc.

After removal of the alpha-amino protecting group, the remaining protected amino acids are coupled stepwise in the desired order. An excess of each protected amino acid is generally used with an appropriate carboxyl group activator such as dicyclohexylcarbodiimide (DCC) in solution, for example, in methylene chloride ($CH_2Cl_2$), dimethyl formamide (DMF) mixtures.

After the desired amino acid sequence has been completed, the desired peptide is decoupled from the resin support by treatment with a reagent such as trifluoroacetic acid or hydrogen fluoride (HF), which not only cleaves the peptide from the resin, but also cleaves all remaining side chain protecting groups. When the chloromethylated resin is used, hydrogen fluoride treatment results in the formation of the free peptide acids. When the benzhydrylamine resin is used, hydrogen fluoride treatment results directly in the free peptide amide.

Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides.

These solid phase peptide synthesis procedures are well known in the art and further described by Stewart and Young, *Solid Phase Peptide Syntheses* (2nd Ed., Pierce Chemical Company, 1984).

B. Synthetic Amino Acids

These procedures can also be used to synthesize peptides in which amino acids other than the 20 naturally occurring, genetically encoded amino acids are substituted at one, two, or more positions of any of the compounds described herein. For instance, naphthylalanine can be substituted for tryptophan, facilitating synthesis. Other synthetic amino acids that can be substituted into the peptides include L-hydroxypropyl, L-3,4-dihydroxy-phenylalanyl, amino acids such as L-d-hydroxylysyl and D-d-methylalanyl, L-α-methylalanyl, β amino acids, and isoquinolyl. D amino acids and non-naturally occurring synthetic amino acids can also be incorporated into the peptides.

One can replace the naturally occurring side chains of the 20 genetically encoded amino acids (or D amino acids) with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered hetereocyclic. In particular, proline analogs in which the ring size of the proline residue is changed from 5 members to 4, 6, or 7 members can be employed. Cyclic groups can be saturated or unsaturated, and if unsaturated, can be aromatic or non-aromatic. Heterocyclic groups preferably contain one or more nitrogen, oxygen, and/or sulphur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl. These heterocyclic groups can be substituted or unsubstituted. Where a group is substituted, the substituent can be alkyl, alkoxy, halogen, oxygen, or substituted or unsubstituted phenyl.

One can also readily modify the peptides by phosphorylation (see, e.g., Bannwarth et al. 1996 *Biorganic and Medicinal Chemistry Letters* 6:2141-2146), and other methods for making peptide derivatives of the compounds disclosed herein are described in Hruby et al. 1990 *Biochem J* 268:249-262. Thus, the peptide compounds can also serve as a basis to prepare peptide mimetics with similar biological activity.

C. Terminal Modifications

Those of skill in the art recognize that a variety of techniques are available for constructing peptide mimetics with the same or similar desired biological activity as the corresponding peptide compound but with more favorable activity than the peptide with respect to solubility, stability, and susceptibility to hydrolysis and proteolysis. See, e.g., Morgan et al. 1989 *Ann Rep Med Chem* 24:243-252. The following describes methods for preparing peptide mimetics modified at the N-terminal amino group, the C-terminal carboxyl group, and/or changing one or more of the amido linkages in the peptide to a non-amido linkage. It being understood that two or more such modifications can be coupled in one peptide mimetic structure (e.g., modification at the C-terminal carboxyl group and inclusion of a —$CH_2$-carbamate linkage between two amino acids in the peptide).

1. N-Terminal Modifications

The peptides typically are synthesized as the free acid but, as noted above, could be readily prepared as the amide or ester. One can also modify the amino and/or carboxy terminus of the peptide compounds to produce other compounds. Amino terminus modifications include methylation (i.e., —$NHCH_3$ or —$NH(CH_3)_2$), acetylation, adding a benzyloxycarbonyl group, or blocking the amino terminus with any blocking group containing a carboxylate functionality defined by RCOO—, where R is selected from the group consisting of naphthyl, acridinyl, steroidyl, and similar groups. Carboxy terminus modifications include replacing the free acid with a carboxamide group or forming a cyclic lactam at the carboxy terminus to introduce structural constraints.

Amino terminus modifications are as recited above and include alkylating, acetylating, adding a carbobenzoyl group, forming a succinimide group, etc. (see, e.g., Murray et al., *Burger's Medicinal Chemistry and Drug Discovery*, 5th Ed., Vol. 1, Wolf, ed., John Wiley and Sons, Inc. (1995)) Specifically, the N-terminal amino group can then be reacted as follows:

a) to form an amide group of the formula RC(O)NH— where R is as defined above by reaction with an acid halide (e.g., RC(O)Cl) or symmetric anhydride. Typically, the reaction can be conducted by contacting about equimolar or excess amounts (e.g., about 5 equivalents) of an acid halide to the peptide in an inert diluent (e.g., dichloromethane) preferably containing an excess (e.g., about 10 equivalents) of a tertiary amine, such as diisopropylethylamine, to scavenge the acid generated during reaction. Reaction conditions are otherwise conventional (e.g., room temperature for 30 minutes). Alkylation of the terminal amino to provide for a lower alkyl N-substitution followed by reaction with an acid halide as described above will provide for N-alkyl amide group of the formula RC(O)NR—; or b) to form a succinimide group by reaction with succinic anhydride. As before, an approximately equimolar amount or an excess of succinic anhydride (e.g., about 5 equivalents) can be employed and the amino group is converted to the succinimide by methods well known in the art including the use of an excess (e.g., ten equivalents) of a tertiary amine such as diisopropylethylamine in a suitable inert solvent (e.g., dichloromethane). See, for example, Wollenberg et al. U.S. Pat. No. 4,612,132 which is incorporated herein by reference in its entirety. It is understood that the succinic group can be substituted with, for example, $C_2$-$C_6$ alkyl or —SR substituents which are prepared in a conventional manner to provide for substituted succinimide at the N-terminus of the peptide. Such alkyl substituents are prepared by reaction of a lower olefin ($C_2$—C) with maleic anhydride in the manner described by Wollenberg et al., supra and —SR substituents are prepared by reaction of RSH with maleic anhydride where R is as defined above; or c) to form a benzyloxycarbonyl-NH— or a substituted benzyloxycarbonyl-NH— group by reaction with approximately an equivalent amount or an excess of CBZ-Cl (i.e., benzyloxycarbonyl chloride) or a substituted CBZ-Cl in a suitable inert diluent (e.g., dichloromethane) preferably containing a tertiary amine to scavenge the acid generated during the reaction; or d) to form a sulfonamide group by reaction with an equivalent amount or an excess (e.g., 5 equivalents) of R—S(O)$_2$Cl in a suitable inert diluent (dichloromethane) to convert the terminal amine into a sulfonamide where R is as defined above. Preferably, the inert diluent contains excess tertiary amine (e.g., ten equivalents) such as diisopropylethylamine, to scavenge the acid generated during reaction. Reaction conditions are otherwise conventional (e.g., room temperature for 30 minutes); or e) to form a carbamate group by reaction with an equivalent amount or an excess (e.g., 5 equivalents) of R—OC(O)Cl or R—OC(O)OC$_6$H$_4$-p-NO$_2$ in a suitable inert diluent (e.g., dichloromethane) to convert the terminal amine into a carbamate where R is as defined above. Preferably, the inert diluent contains an excess (e.g., about 10 equivalents) of a tertiary amine, such as diisopropylethylamine, to scavenge any acid generated during reaction. Reaction conditions are otherwise conventional (e.g., room temperature for 30 minutes); or f) to form a urea group by reaction with an equivalent amount or an excess (e.g., 5 equivalents) of R—N=C=O in a suitable inert diluent (e.g., dichloromethane) to convert the terminal amine into a urea (i.e., RNHC(O)NH—) group where R is as defined above. Preferably, the inert diluent contains an excess (e.g., about 10 equivalents) of a tertiary amine, such as diisopropylethylamine. Reaction conditions are otherwise conventional (e.g., room temperature for about 30 minutes).

2. C-Terminal Modifications

In preparing peptide mimetics wherein the C-terminal carboxyl group is replaced by an ester (i.e., —C(O)OR where R is as defined above), the resins used to prepare the peptide acids are employed, and the side chain protected peptide is cleaved with base and the appropriate alcohol, e.g., methanol. Side chain protecting groups are then removed in the usual fashion by treatment with hydrogen fluoride to obtain the desired ester.

In preparing peptide mimetics wherein the C-terminal carboxyl group is replaced by the amide —C(O)NR$^3$R$^4$, a benzhydrylamine resin is used as the solid support for peptide synthesis. Upon completion of the synthesis, hydrogen fluoride treatment to release the peptide from the support results directly in the free peptide amide (i.e., the C-terminus is —C(O)NH$_2$). Alternatively, use of the chloromethylated resin during peptide synthesis coupled with reaction with ammonia to cleave the side chain protected peptide from the support yields the free peptide amide and reaction with an alkylamine or a dialkylamine yields a side chain protected alkylamide or dialkylamide (i.e., the C-terminus is —C(O)NRR$^1$ where R and R$^1$ are as defined above). Side chain protection is then removed in the usual fashion by treatment with hydrogen fluoride to give the free amides, alkylamides, or dialkylamides.

In another alternative embodiment, the C-terminal carboxyl group or a C-terminal ester can be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride (CH$_2$Cl$_2$), dimethyl formamide (DMF) mixtures. The cyclic peptide is then formed by internal displacement of the activated ester with the N-terminal amine. Internal cyclization as opposed to polymerization can be enhanced by use of very dilute solutions. Such methods are well known in the art.

One can also cyclize the peptides herein, or incorporate a desamino or descarboxy residue at the termini of the peptide, so that there is no terminal amino or carboxyl group, to decrease susceptibility to proteases or to restrict the conformation of the peptide. C-terminal functional groups of the compounds include amide, amide lower alkyl, amide di(lower alkyl), lower alkoxy, hydroxy, and carboxy, and the lower ester derivatives thereof, and the pharmaceutically acceptable salts thereof.

In addition to the foregoing N-terminal and C-terminal modifications, the peptide compounds, including peptidomimetics, can advantageously be modified with or covalently coupled to one or more of a variety of hydrophilic polymers. It has been found that when the peptide compounds are derivatized with a hydrophilic polymer, their solubility and circulation half-lives are increased and their immunogenicity is masked. Quite surprisingly, the foregoing can be accomplished with little, if any, diminishment in their binding activity. Nonproteinaceous polymers suitable for use include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives, etc. Generally, such hydrophilic polymers have an average molecular weight ranging from about 500 to about 100,000 daltons, more preferably from about 2,000 to about 40,000 daltons and, even more preferably, from about 5,000 to about 20,000 daltons. In preferred embodiments, such hydrophilic polymers have an average molecular weights of about 5,000 daltons, 10,000 daltons and 20,000 daltons.

The peptide compounds can be derivatized with or coupled to such polymers using, but not limited to, any of the methods set forth in Zallipsky 1995 *Bioconjugate Chem* 6:150-165 and Monfardini et al. 1995 *Bioconjugate Chem* 6:62-69, all of which are incorporated by reference in their entirety herein.

In a presently preferred embodiment, the peptide compounds are derivatized with polyethylene glycol (PEG). PEG is a linear, water-soluble polymer of ethylene oxide repeating units with two terminal hydroxyl groups. PEGs are classified by their molecular weights which typically range from about 500 daltons to about 40,000 daltons. In a presently preferred embodiment, the PEGs employed have molecular weights ranging from 5,000 daltons to about 20,000 daltons. PEGs coupled to the peptide compounds can be either branched or unbranched. (see, e.g., Monfardini et al. 1995 *Bioconjugate Chem* 6:62-69). PEGs are commercially available from Shearwater Polymers, Inc. (Huntsville, Ala.), Sigma Chemical Co. and other companies. Such PEGs include, but are not limited to, monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH$_2$), monomethoxypolyethylene glycol-tresylate (MePEG-TRES), and monomethoxypolyethylene glycol-imidazolyl-carbonyl (MePEG-IM).

Briefly, in one exemplar embodiment, the hydrophilic polymer which is employed, e.g., PEG, is preferably capped at one end by an unreactive group such as a methoxy or ethoxy group. Thereafter, the polymer is activated at the other end by reaction with a suitable activating agent, such as cyanuric halides (e.g., cyanuric chloride, bromide or fluoride), diimadozle, an anhydride reagent (e.g., a dihalosuccinic anhydride, such as dibromosuccinic anhydride), acyl azide, p-diazoiumbenzyl ether, 3-(p-diazoniumphenoxy)-2-hydroxypropylether) and the like. The activated polymer is then reacted with a peptide compound disclosed or taught herein to produce a peptide compound derivatized with a polymer. Alternatively, a functional group in the peptide compounds can be activated for reaction with the polymer, or the two groups can be joined in a concerted coupling reaction using known coupling methods. It will be readily appreciated that the peptide compounds can be derivatized with PEG using a myriad of reaction schemes known to and used by those of skill in the art.

In addition to derivatizing the peptide compounds with a hydrophilic polymer (e.g., PEG), it has been discovered that other small peptides, e.g., other peptides or ligands that bind to a receptor, can also be derivatized with such hydrophilic polymers with little, if any, loss in biological activity (e.g., binding activity, agonist activity, antagonist activity, etc.). It has been found that when these small peptides are derivatized with a hydrophilic polymer, their solubility and circulation half-lives are increased and their immunogenicity is decreased. Again, quite surprisingly, the foregoing can be accomplished with little, if any, loss in biological activity. In fat, in preferred embodiments, the derivatized peptides have an activity that is 0.1 to 0.01-fold that of the unmodified peptides. In more preferred embodiments, the derivatized peptides have an activity that is 0.1 to 1-fold that of the unmodified peptides. In even more preferred embodiments, the derivatized peptides have an activity that is greater than the unmodified peptides.

Peptides suitable for use in this embodiment generally include those peptides, i.e., ligands that bind to members of the Bcl-2 receptor family. Such peptides typically comprise about 150 amino acid residues or less and, more preferably, about 100 amino acid residues or less (e.g., about 10-12 kDa). Hydrophilic polymers suitable for use herein include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives, etc. Generally, such hydrophilic polymers have an average molecular weight ranging from about 500 to about 100,000 daltons, more preferably from about 2,000 to about 40,000 daltons and, even more preferably, from about 5,000 to about 20,000 daltons. In preferred embodiments, such hydrophilic polymers have an average molecular weights of about 5,000 daltons, 10,000 daltons and 20,000 daltons. The peptide compounds can be derivatized with using the methods described above and in the cited references.

D. Backbone Modifications

Other methods for making peptide derivatives of the compounds described herein are described in Hruby et al. 1990 *Biochem J* 268:249-262, incorporated herein by reference. Thus, the peptide compounds also serve as structural models for non-peptidic compounds with similar biological activity. Those of skill in the art recognize that a variety of techniques are available for constructing compounds with the same or similar desired biological activity as the lead peptide compound but with more favorable activity than the lead with respect to solubility, stability, and susceptibility to hydrolysis and proteolysis. See Morgan et al., 1989, *Ann Rep Med Chem* 24:243-252, incorporated herein by reference. These techniques include replacing the peptide backbone with a backbone composed of phosphonates, amidates, carbamates, sulfonamides, secondary amines, and N-methylamino acids.

Peptide mimetics wherein one or more of the peptidyl linkages [—C(O)NH—] have been replaced by such linkages as a —$CH_2$-carbamate linkage, a phosphonate linkage, a —$CH_2$-sulfonamide linkage, a urea linkage, a secondary amine (—$CH_2$NH—) linkage, and an alkylated peptidyl linkage [—C(O)NR— where $R^6$ is lower alkyl] are prepared during conventional peptide synthesis by merely substituting a suitably protected amino acid analogue for the amino acid reagent at the appropriate point during synthesis.

Suitable reagents include, for example, amino acid analogues wherein the carboxyl group of the amino acid has been replaced with a moiety suitable for forming one of the above linkages. For example, if one desires to replace a —C(O)NR— linkage in the peptide with a —$CH_2$-carbamate linkage (—$CH_2$OC(O)NR—), then the carboxyl (—COOH) group of a suitably protected amino acid is first reduced to the —$CH_2$OH group which is then converted by conventional methods to a —OC(O)Cl functionality or a para-nitrocarbonate —OC(O)O—$C_6H_4$-p-$NO_2$ functionality. Reaction of either of such functional groups with the free amine or an alkylated amine on the N-terminus of the partially fabricated peptide found on the solid support leads to the formation of a —$CH_2$OC(O)NR— linkage. For a more detailed description of the formation of such —$CH_2$-carbamate linkages, see Cho et al. 1993 *Science* 261:1303-1305.

Similarly, replacement of an amido linkage in the peptide with a phosphonate linkage can be achieved in the manner set forth in U.S. patent application Ser. Nos. 07/943,805, 08/081,577 and 08/119,700, the disclosures of which are incorporated herein by reference in their entirety.

Replacement of an amido linkage in the peptide with a —$CH_2$-sulfonamide linkage can be achieved by reducing the carboxyl (—COOH) group of a suitably protected amino acid to the —$CH_2$OH group and the hydroxyl group is then converted to a suitable leaving group such as a tosyl group by conventional methods. Reaction of the tosylated derivative with, for example, thioacetic acid followed by hydrolysis and oxidative chlorination will provide for the —$CH_2$—$S(O)_2$Cl functional group which replaces the carboxyl group of the otherwise suitably protected amino acid. Use of this suitably protected amino acid analogue in peptide synthesis provides for inclusion of an —$CH_2S(O)_2$NR— linkage which replaces the amido linkage in the peptide thereby providing a peptide mimetic. For a more complete description on the conversion of the carboxyl group of the amino acid to a —$CH_2S(O)_2$Cl group, see, for example, Weinstein, *Chemistry & Biochemistry of Amino Acids, Peptides and Proteins*, Vol. 7, pp. 267-357, Marcel Dekker, Inc., New York (1983) which is incorporated herein by reference.

Replacement of an amido linkage in the peptide with a urea linkage can be achieved in the manner set forth in U.S. patent application Ser. No. 08/147,805, which is incorporated herein by reference.

Secondary amine linkages wherein a $CH_2$NH linkage replaces the amido linkage in the peptide can be prepared by employing, for example, a suitably protected dipeptide analogue wherein the carbonyl bond of the amido linkage has been reduced to a $CH_2$ group by conventional methods. For example, in the case of diglycine, reduction of the amide to the amine will yield after deprotection $H_2NCH_2CH_2NHCH_2COOH$ which is then used in N-protected form in the next coupling reaction. The preparation of such analogues by reduction of the carbonyl group of the amido linkage in the dipeptide is well known in the art (see, e.g., Remington 1994 *Meth Mol Bio* 35:241-247).

The suitably protected amino acid analogue is employed in the conventional peptide synthesis in the same manner as would the corresponding amino acid. For example, typically about 3 equivalents of the protected amino acid analogue are employed in this reaction. An inert organic diluent such as methylene chloride or DMF is employed and, when an acid is generated as a reaction by-product, the reaction solvent will typically contain an excess amount of a tertiary amine to scavenge the acid generated during the reaction. One particularly preferred tertiary amine is diisopropylethylamine which is typically employed in about 10 fold excess. The reaction results in incorporation into the peptide mimetic of an amino acid analogue having a non-peptidyl linkage. Such substitution can be repeated as desired such that from zero to all of the amido bonds in the peptide have been replaced by non-amido bonds.

One can also cyclize the peptides described herein, or incorporate a desamino or descarboxy residue at the termini of the peptide, so that there is no terminal amino or carboxyl group, to decrease susceptibility to proteases or to restrict the conformation of the peptide. C-terminal functional groups of the compounds include amide, amide lower alkyl, amide di(lower alkyl), lower alkoxy, hydroxy, and carboxy, and the lower ester derivatives thereof, and the pharmaceutically acceptable salts thereof.

E. Disulfide Bond Formation

The compounds described herein may exist in a cyclized form with an intramolecular disulfide bond between the thiol groups of the cysteines. Alternatively, an intermolecular disulfide bond between the thiol groups of the cysteines can be produced to yield a dimeric (or higher oligomeric) compound. One or more of the cysteine residues may also be substituted with a homocysteine.

Other embodiments of this invention provide for analogs of these disulfide derivatives in which one of the sulfurs has been replaced by a $CH_2$ group or other isostere for sulfur. These analogs can be made via an intramolecular or intermolecular displacement, using methods known in the art.

Alternatively, the amino-terminus of the peptide can be capped with an alpha-substituted acetic acid, wherein the alpha substituent is a leaving group, such as an α-haloacetic acid, for example, α-chloroacetic acid, α-bromoacetic acid, or α-iodoacetic acid.

The compounds can be cyclized or dimerized via displacement of the leaving group by the sulfur of the cysteine or homocysteine residue. See, e.g., Andreu et al. 1994 *Meth Mol Bio* 35:91-169; Barker et al. 1992 *J Med Chem* 35:2040-2048; and Or et al. 1991 *J Org Chem* 56:3146-3149, each of which is incorporated herein by reference.

The present peptides may also be prepared by recombinant DNA techniques well known in the art.

IV. Antibody Preparation

Antibodies against the loop domain of Bcl-2. The N-terminal loop region of Bcl-2 can be expressed and used as an antigen to develop anti-Bcl-2/N-terminal loop region antibodies. These antibodies, by binding to the loop domain of Bcl-2, can mimic the activity of TR3 in the induction of a conformational change of Bcl-2 which will expose the hidden BH3 domain and confer pro-apoptotic activity to the Bcl-2 protein.

Further, Bcl-$X_L$ can be expressed and used as an antigen to develop anti-Bcl-$X_L$ antibodies. Antibodies which mimic the activity of TCTP may be identified. The antibodies may then be used for therapeutics and diagnostics comparably to those identified for Bcl-2.

The terms "antibody" or "antibody peptide(s)" refer to an intact antibody, or a binding fragment thereof that competes with the intact antibody for specific binding. Binding fragments are produced by recombinant DNA techniques, or by enzymatic or chemical cleavage of intact antibodies. Binding fragments include Fab, Fab', F(ab')$_2$, Fv, and single-chain antibodies. An antibody other than a "bispecific" or "bifunctional" antibody is understood to have each of its binding sites identical. An antibody substantially inhibits adhesion of a receptor to a counterreceptor when an excess of antibody reduces the quantity of receptor bound to counterreceptor by at least about 20%, 40%, 60% or 80%, and more usually greater than about 85% (as measured in an in vitro competitive binding assay).

The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is $\leq 1$ µM, preferably $\leq 100$ nM and most preferably $\leq 10$ nM.

Antibody Structure

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989), incorporated by reference in its entirety for all purposes. The variable regions of each light/heavy chain pair form the antibody binding site. Thus, an intact antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk *J. Mol. Biol.* 196:901-917 (1987); Chothia et al. *Nature* 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann 1990 *Clin. Exp. Immunol.* 79: 315-321; Kostelny et al. 1992 *J. Immunol.* 148:1547-1553. Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

Human Antibodies and Humanization of Antibodies—Human antibodies avoid certain of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated using methods well known to those of skill in the art.

Therapeutic Administration and Formulations—It will be appreciated that therapeutic entities will be administered with suitable carriers, excipients, and other agents that are incorporated into formulations to provide improved transfer, delivery, tolerance, and the like. A multitude of appropriate formulations can be found in the formulary known to all pharmaceutical chemists: *Remington's Pharmaceutical Sciences* (18$^{th}$ ed, Mack Publishing Company, Easton, Pa. (1990)), particularly Chapter 87 by Block, Lawrence, therein. These formulations include, for example, powders, pastes, ointments, jellies, waxes, oils, lipids, lipid (cationic or anionic) containing vesicles (such as LIPOFECTIN®), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures can be appropriate in treatments and therapies, provided that the active ingredient in the formulation is not inactivated by the formulation and the formulation is physiologically compatible and tolerable with the route of administration. See also Baldrick P. "Pharmaceutical excipient development: the need for preclinical guidance." 2000 *Regul Toxicol Pharmacol* 32:210-8; Wang W. "Lyophilization and development of solid protein pharmaceuticals." 2000 *Int. J. Pharm.* 203:1-60; Charman W N "Lipids, lipophilic drugs, and oral drug delivery-some emerging concepts." 2000 *J Pharm Sci* 89:967-78; Powell et al. "Compendium of excipients for parenteral formulations" 1998 *PDA J Pharm Sci Technol* 52:238-311 and the citations therein for additional information related to formulations, excipients and carriers well known to pharmaceutical chemists.

For diagnostic uses, any type of label (detectable moiety) may be added to the antibody, including but not limited to, for example, a radiolabel, fluorescent label, enzymatic label chemiluminescent label or a biotinyl group. Radioisotopes or radionuclides can include $^3$H, $^{14}$C, $^{15}$N, $^{35}$S, $^{90}$Y, $^{99}$Tc, $^{111}$In, $^{125}$I, $^{131}$I, fluorescent labels can include rhodamine, lanthanide phosphors or FITC and enzymatic labels can include horseradish peroxidase, β-galactosidase, luciferase, alkaline phosphatase.

V. Intrabody Preparation

Intrabodies are scFvs that are expressed within the cell and directed against intracellular proteins. In this way they can interfere and inhibit cellular processes inside the cell in a number of ways. Intrabodies can inhibit an enzymatic activity directly, or interfere with protein-protein interactions, thus disrupting signaling pathways. They can also be used to displace a protein from its site of action. The fusion of intracellular localization signals, such as a nuclear localization signal (NLS) or a retention signal for the endoplasmic reticulum (ER), can be used to re-direct the antibody and its target antigen to specific locations within the cell. For instance, a scFv directed against the ErbB-2 receptor and designed to prevent transit through the ER was shown to down-regulate the surface expression of ErbB-2 and consequently, to considerably affect growth factor signaling.

Thus, it is envisioned that intrabodies can be used to mimic the action of TR3 in a cell to cause apoptosis. Alternatively, intrabodies can be used to interfere with TR3 binding to Bcl-2 to keep cells in a proliferative state. Intrabodies could be advantageously used for the treatment of leukemias and lymphomas because it can be envisioned that the involved blood cells could be more easily removed from a patient, genetically manipulated to include the intrabody, and introduced back into the body of the patient.

Methods of selection of intrabodies includes the use of phage display libraries, ribosome and mRNA display, protein fragment complementation assay (PCA), and yeast screening assays which are an adaptation of the two hybrid system using scFvs and an antigen.

EXAMPLES

The following examples describe the processes used to identify and characterize peptides that target Bcl-2-family members and regulate their apoptotic functions. Unless otherwise indicated, the plasmids and methods were as follows:

Plasmids—Plasmids encoding TR3 and TR3/ΔDBD (Li, et al. 2000 *Science* 289:1159-1164), Bcl-2, Bcl-Gs, L216E-Bcl-Gs, Bcl-2/Δloop (Cheng et al. 1997 *Science* 278:1966-1968), Bax, and Bcl-X$_L$ (Guo, et al. 2001 *J. Biol. Chem.* 276:2780-2785), have been described previously. To construct N168, DC3, DC1, TR3/ΔDBD/DC1, TR3/ΔDBD/A471-488, Bcl-2/1-80, appropriate TR3 or Bcl-2 fragments were prepared either by restriction enzyme digestion or amplified by polymerase chain reaction (PCR). The resulting TR3 fragments were then cloned into pGFP-N2 vector (Clontech, USA). TR3/ΔDBD/L487A were cloned by substituting Leu487 with Ala by PCR site-directed mutagenesis on the TR3/ΔDBD template. Bcl-2/Y108K, Bcl-2/L137A, Bcl-2/G145A, and Bcl-2/R146 were constructed by substituting Tyr108, Leu137, Gly145 and Arg146 with Lys, Ala, Ala, and Glu, respectively, by PCR site-directed mutagenesis using the Bcl-2 cDNA as a template. Bcl2/ΔBH1, Bcl-2/ΔBH2, Bcl-2/ΔBH3, Bcl-2/ΔBH4, Bcl-2/ΔTM are deletions of 132-160, 189-204, 90-114, 7-30, 205-239 amino acids in Bcl-2 (Hanada et al. 1995 *J Biol Chem* 270:11962-11969). All mutations were confirmed by DNA sequencing.

Bcl-2 siRNAs and antisense oligonucleotides—The target siRNA SMARTPOOLs® for Bcl-2 and Bak and the siRNA oligonucleotide for TR3 (5'-CAG UCC AGC CAU GCU CCU dTdT) (SEQ ID NO: 2) were purchased from Dharmacon Research Inc. Target or control siRNA were transfected at a final concentration of 200 nM into cells at 40% confluency using Oligofectamine reagent (Invitrogen) according to the manufacturer's recommendations. After 48 h, cells were analyzed. Bcl-2 antisense oligonucleotide targeting Bcl-2 and negative control oligonucleotides were obtained from Calbiochem. They (2.5 μM) were transfected into cells at 60% confluency for 36 h before analysis.

TR3/Bcl-2 interaction assays—Reporter gene assays using NurRE-tk-CAT in CV-1 cells, and GST pull-down assay were described previously (Li, et al. 2000 Science 289, 1159-1164). For the mammalian two-hybrid assays, CV-1 cells were co-transfected with pcDNA-Gal4TAD-TR3 or pcDNA-Gal4TAD-TR3/ΔDBD and pcDNA-Gal4 DBD-Bcl-2/ΔTM along with a luciferase reporter gene driven by four copies of the Gal4-binding site. The cells were harvested and reporter gene activity was measured. For Co-IP assays, HEK293T cells were transiently transfected with various expression plasmids using a modified calcium phosphate precipitation method (Wu et al, 1997) in the presence of caspase inhibitors (zVAD-fmk) to prevent degradation of TR3 protein due to apoptosis. Cells were suspended in lysis buffer (50 mM Tris-HCl, PH7.4; 150 mM NaCl; 20 mM EDTA; 1% NP-40; 1 mM PMSF; 50 µg/ml Leupeptin; 20 mg/ml Aprotinin; 0.1 mM $Na_3VO_4$; and 1 mM DTT). Cells extracts were cleared by incubation with the Protein A/G plus Agarose beads (Santa Cruz) and then incubated with appropriate antibody and 30 µl of Protein A or G plus Agarose beads overnight at 4° C. Beads were then washed and boiled in Laemmli gel-loading solution before performing SDS-PAGE/immunoblotting using the following polyclonal or monoclonal antibodies: monoclonal mouse anti-GFP (Medical and Biological Laboratories), monoclonal mouse anti-HA (Roche Molecular Biochemicals), monoclonal mouse anti-FLAG (Sigma), monoclonal mouse anti-Myc (Santa Cruz), polyclonal rabbit anti-TR3 (Active Motif), or monoclonal mouse anti-Bcl-2 (Santa Cruz). Immunoreactive products were detected by chemiluminescence with an enhanced chemiluminescence system (ECL) (Amersham).

Subcellular localization assays—Cells were seeded onto cover-slips in 6-well plates overnight, then transiently transfected with GFP-fusion expression plasmids. After 16 hours, cells were washed with PBS and fixed in 4% paraformaldehyde. For mitochondrial staining, cells were then incubated with anti-Hsp60 goat IgG (Santa Cruz, USA), followed by anti-goat IgG conjugated with Cy3 (Sigma). For cyt c staining, cells were incubated with monoclonal anti-cyt c IgG (PharMingen), followed by anti-mouse IgG conjugated with Cy5 (Amersham). Fluorescent images were collected and analyzed using a MRC-1024 MP laser-scanning confocal microscope (Bio-Rad). Subcellular fractionation assays were performed as described (Li, et al. 2000 *Science* 289:1159-1164). Briefly, cells ($1\times10^7$ cells) suspended in 0.5 ml hypotonic buffer (5 mM Tris-HCl, pH 7.4, 5 mM KCl, 1.5 mM $MgCl_2$, 0.1 mM EGTA, pH 8.0, and 1 mM DTT) were homogenized and cell extracts were centrifuged at 500×g for 5 min. The resulting supernatant was centrifuged at 10,000×g for 30 min at 4° C. to obtain the HM fraction. HM fraction was resuspended in 100 µl lysis buffer (10 mM Tris, pH 7.4, 150 mM NaCl, 1% Triton X-100, 5 mM EDTA, pH 8.0) for immunoblotting analysis.

Apoptosis assays—For nuclear morphological change analysis, cells were trypsinized, washed with PBS, fixed with 3.7% paraformaldehyde, and stained with DAPI (4,6-diamidino-2-phenylindole) (50 µg/ml) to visualize the nuclei by UV-microscopy. The percentages of apoptotic cells were determined by counting 300 GFP-positive cells, scoring cells having nuclear fragmentation and/or chromatin condensation.

Isolation and transfection of human peripheral blood lymphocytes (PBLs)—Leukocyte-enriched buffy coats from San Diego Blood Bank were diluted with 2 volumes of PBS, and PBLs were isolated by centrifuge on Ficoll-paque™ Plus (Amersham Pharmacia biotech). The mononuclear cells were cultured in RPMI containing 10% FBS and 20 µM Hepes. Freshly isolated cells ($10^7$ cells per transfection) were washed once with PBS containing 0.5% BSA and supernatant was completely discarded so that no residual PBS/BSA covers the pellet. The cells were resuspended in 100 µl of the human T Cell Nucleofector™ solution (Amexa biosystems) and very gently mixed with 1-4 µg DNA in 5 µl. The cell suspension was transferred into a cuvette supplied by Amexa biosystems and electroporated using U-14 program of Nucleoftorm device. The cells were removed from the cuvette quickly by adding 500 µl of the pre-warmed RPMI medium containing 10% FBS and 20 µM Hepes and transferred into 12 well plates containing 1.5 ml of pre-warmed culture medium.

Example 1

AHPN, TR3 and Apoptosis in Prostate, Lung and Breast Cancer Cells

Retinoid AHPN (6-[3-(1-adamantyl)-4-hydroxyphenyl]-2-naphthalenecarboxylic acid) potently induces apoptosis of prostate cancer cells by inducing translocation of TR3 from the nucleus to mitochondria (Li et al. 2000 *Science* 289:1159-1164). AHPN and its analogs also effectively induce apoptosis of lung and breast cancer cells (Li et al. 1998 *Mol Cell Bio* 18:4719-4731; Shao et al. 1995 *Oncogene* 11:493-504). TR3 expression was significantly induced by AHPN in lung cancer cells. Moreover, inhibition of TR3 expression by overexpressing TR3 antisense RNA abolished apoptosis by AHPN, indicating that TR3 is essential for AHPN-induced apoptosis of lung cancer cells (Li et al. 1998, supra).

Given the results of these studies, it was desirable to determine whether TR3 exerts its apoptotic effect in lung cancer cells as in prostate cancer cells by targeting to mitochondria. GFP-TR3/ΔDBD (a TR3 mutant that lacks the DNA-binding domain) was transiently transfected into NCI-H460 lung cancer cells. The cells were stained for mitochondria (Hsp60) and cytochrome c (Cyt c), and analyzed by confocal microscopy. GFP-TR3/ΔDBD expressed in lung cancer cells displaced a distribution pattern overlaid extensively with that of heat shock protein 60 (HSP60), a mitochondrial specific protein. These data indicate that GFP-TR3/ΔDBD targeted to mitochondria in lung cancer cells, as it did in prostate cancer cells.

TR3 is also expressed in both estrogen-dependent ZR-75-1 and in estrogen-independent MDA-MB-231 breast cancer cells (Wu et al. 1997 *Mol Cell Bio* 17:6598-6608). It was previously shown that AHPN effectively induces apoptosis of both types of breast cancer cell lines. To determine whether TR3 also mediated the apoptotic effect of AHPN and its analogs in breast cancer cells, MDA-MB-231 breast cancer cells were treated with MM11453, which effectively induces apoptosis of estrogen-dependent and -independent breast cancer cells. Total RNAs were prepared from MDA-MB-231 cells treated with MM1153 ($10^{-6}$M), MM11384 ($10^{-6}$M), TPA (100 ng/ml) or EGF (200 ng/ml) for 3 h. and analyzed by Northern blotting. Upon MM11453 treatment, TR3 expression in MDA-MB-231 cells was significantly induced. TR3 expression was also induced by another apoptosis-inducing retinoid (MM11384), TPA, and the mitogenic agent epidermal growth factor (EGF).

To study whether the TR3 nuclear-to-mitochondrial targeting pathway also occurs in breast cancer cells, a GFP-TR3 fusion construct was transfected into MDA-MB-231 cells. GFP-TR3-transfected MDA-MB231 cells were treated with or without MM11453 ($10^{-6}$M) or MM11384 ($10^{-6}$ M) for 1 hour, then immunostained with anti-Hsp60 antibody (Sigma) followed by Cy3-conjugated secondary antibody (Sigma) to detect mitochondria. GFP-TR3 and mitochondria (Hsp60) were visualized using confocal microscopy and the two images were overlaid. The GFP-TR3 fusion protein was predominately present in the nucleus in nonstimulated cells. However, upon treatment with MM11453 and MM11384, GFP-TR3 translocated to mitochondria. Next, GFP-TR3/ΔDBD was transiently transfected into ZR-75-1 or MDA-MB-231 cells, stained for mitochondria (Hsp60) and cytochrome c (Cyt c), and analyzed by confocal microscopy. GFP-TR3/ΔDBD was targeted to mitochondria of MDA- MB-231 and ZR-75-1 cells in the absence of any treatment and caused release of cytochrome c from the mitochondria.

Cellular localization of TR3 expressed in mammary tumor derived from transgenic mice bearing polyomavirus middle T antigen, was also studied (provided by Dr. W. Muller, see Hutchinson et al. 2001 *Mol Cell Bio* 21:2203-2212). The tissue sample was analyzed by the TdT assay for apoptosis. Mammary tumor tissue from transgenic mice bearing polyomavirus middle T antigen was stained with TR3 followed by Cy3-conjugated secondary antibody to detect TR3 expression and subcellular localization by confocal microscopy. The tissue was also analyzed by the fluorescein conjugated TdT enzyme (Oncogene) to detect DNA fragmentation (TdT-labeled cells are indicated by green color). Two images were overlaid to assess the correlation between apoptosis and TR3 subcellular localization. The result showed that TR3 was localized in the cytoplasm in cells undergoing extensive apoptosis, while it was found in the nucleus in nonapoptotic cells. Thus, subcellular localization of TR3 plays a role in regulating mammary tumor cell apoptosis.

Example 2

Interaction of TR3 with Bcl-2

The possibility that TR3 targeted mitochondria by interacting with Bcl-2 was investigated by first identifying whether the two proteins interact directly. This was done using a variety of methods including co-immunoprecipitation assays, protein binding assays, two-hybrid assays, co-localization assays and NurRE-dependent reporter gene assays. In all cases a direct interaction between TR3 and Bcl-2 was identified.

A. co-immunoprecipitation assays—to identify the interaction between TR3 and Bcl-2, a monoclonal antibody was generated against the ligand-binding domain (GBD) of TR3 for co-immunoprecipitation (Co-IP) assays. LNCaP cells were treated with TPA to induce endogenous TR3 expression for 3 hours. Cell extracts were prepared from TPA-treated and non-treated cells and incubated with mouse monoclonal anti-TR3 antibody. Immunoblotting of immunoprecipitates employed anti-Bcl-2 antibody or rabbit polyclonal anti-TR3 anti-body (Active Motif). Bcl-2 was specifically co-immunoprecipitated by anti-TR3 antibody in TPA-treated cells, but not in non-treated cells.

In addition to TPA, AHPN and its structural analogs also induce TR3 expression and TR3-dependent apoptosis in an epithelial cancer cell line. Lysates from H460 lung cancer cells were treated with the AHPN analog 3-Cl-AHPC (also called MM002) at $10^{-6}$ M for 3 hours, which potently induces TR3 expression, mitochondrial targeting and apoptosis in these cells. Lysates were then incubated with anti-Bcl-2 antibody. Immunoblotting of immunoprecipitates was conducted using anti-TR3 and anti-Bcl-2 antibodies. This also demonstrated co-immunoprecipitation of TR3 with anti-Bcl-2 antibody.

TR3/ΔDBD, which can constitutively reside on mitochondria, was also analyzed by co-immunoprecipitation (Co-IP) assay for its interaction with Bcl-2. GFP-TR3/ΔDBD was transfected into human embryonic kidney cell line 293T alone or together with a Bcl-2 expression vector. The expressed GFP-TR3/ΔDBD mutant protein as then precipitated by using either anti-Bcl-2 antibody or control IgG and detected by western blotting using anti-GFP antibody. The same membranes were also blotted with anti-Bcl-2 antibody to determine precipitation specificity and efficiency. Input represents 10% of total cell extract used in the precipitation assays. These co-IP assays showed that a significant amount of TR3/ΔDBD was co-precipitated with Bcl-2 by anti-Bcl-2 antibody.

B. NurRE-dependent reporter gene assay. To investigate the inhibition of TR3-dependent transactivation by Bcl-2, a reporter gene assay was performed. CV-1 cells were transfected with the NurRE-tk-CAT (Li et al. Science 289:1159-1164) and the β-gal expression vector (100 ng) with or without TR3 expression vector (25 ng) together and with or without Bcl-2 or BAX expression vector. CAT activity was then determined. Transactivation of TR3 on its responsive element (NurRE-tk-CAT) was potently inhibited by cotransfection of Bcl-2 but not BAX (FIG. 1), confirming the interaction between Bcl-2 and TR3.

C. in vitro protein binding assays. To further investigate the interaction between TR3/ΔDBD and Bcl-2, a GST pull-down assay was performed. GST-TR3, GST or GST-RXR immobilized on 20 μl of glutathione-Sepharose was incubated with 10 μl of in vitro synthesized $^{35}$S-labeled Bcl-2, RXRα, TR3, or Bax (10 μl). Bound proteins were analyzed by SDS-PAGE autoradiography. $^{35}$S-labeled Bcl-2 was pulled down by GST-TR3 but not by GST. RXRα, a known heterodimerization partner of TR3 was also pulled down by GST-TR3. Conversely, $^{35}$S-labeled TR3 and Bax, a known heterodimerization partner of Bcl-2, bound equally to GST-Bcl-2 but not to GST.

D. co-localization in cells—First the interaction of endogenous TR3 and transfected Bcl-2 colocalization was identified in cells. The phorbol ester 12-0-tetradecanoyl phorbol-13-acetate (TPA) induces the expression of endogenous TR3 and its mitochondrial localization in LNCaP prostate cancer cells. LNCaP cells were transfected with Bcl-2 expression vector, treated with or without TPA (100 ng/ml) for 3 h, then immunostained with anti-Bcl-2 antibody (Santa Cruz) followed by Cy5-conjugated secondary antibody (Amersham Biosciences), or with mouse monoclonal anti-TR3 antibody followed by Cy3-conjugated secondary antibody (Sigma). Endogenous TR3 and transfected Bcl-2 were visualized using confocal microscopy and images were overlaid. To demonstrate the mitochondrial localization of TR3 and Bcl-2, cells were also stained with Hsp60 antibody followed by FITC-conjugated secondary antibody and images were overlaid. Approximately 80% of TPA-treated cells demonstrated colocalization. TR3 was not detected prior to TPA treatment. However, strong TR3 immunostaining occurred after treatment. In TPA-stimulated cells, the distribution patterns of endogenous TR3 and transfected Bcl-2 overlapped extensively in the cytoplasm, colocalizing with Hsp60, a mitochondria-specific protein.

Next, the interaction of transfected TR3 and Bcl-2 was analyzed. Expression vectors for GFP-TR3/ΔDBD, (GFP-(DBD) and Bcl-2 were cotransfected into LNCaP cells. After 20 h, cells were immunostained with anti-Bcl-2 antibody followed by Cy3-conjugated secondary antibodies (Sigma). GFP-fusion and Bcl-2 were visualized using confocal microscopy, and the two images were overlaid. For a control, the distribution of transfected GFP empty vector was analyzed. Approximately 30% of transfected cells exhibited colocalization. These studies demonstrated that TR3 interacts specifically with Bcl-2.

E. Two-hybrid assay—a two-hybrid assay was performed to assess the interaction of TR3 and Bcl-2. The C-terminal trans-membrane domain (TM) was deleted from Bcl-2 to prevent its membrane accumulation. Gal4 reporter gene (Gal4)$_2$-tk-CAT (250 ng) and β-gal expression plasmids (50 ng) were co-transfected into CV-1 cells with the Bcl-2/ΔTM lacking the trans-membrane domain or RXRα fused with the Gal4 DNA-binding domain (Gal-DBD) alone or with the TR3 or TR3/ΔDBD fused with the Gal4 transactivation domain (Gal-TAD). Reporter gene activity was determined 48 h later and normalized relative to β-gal activity. Bcl-2/ΔTM fused with the Gal4-DNA-binding domain (DBD) strongly activated a reporter containing a Gal4-response element when co-expressed with the Gal4 transactivation-domain (TAD) fused with TR3 or TR3/ΔDBD, a TR3 mutant lacking its DBD. Comparable activation was observed upon co-transfection of the Gal4-TAD-TR3 fusion with an expression vector containing RXRα fused with Gal4-DBD.

Example 3

The Domain of TR3 which Interacts with Bcl-2

Several TR3 mutants were analyzed to determine the domain of TR3 which interacts with Bcl-2. The TR3 mutants are schematically represented in FIG. 1. A Co-IP assay was performed, as described above. Briefly, plasmids encoding these TR3 mutant GFP fusions were transfected into HEK293T cells, which contained undetectable levels of endogenous Bcl-2, with or without a Bcl-2 expression vector (2 μg) (the empty vector pRC/CMV was used as a control). The empty GFP vector (6 μg) was also used as a control. Cell extracts were prepared and incubated with anti-Bcl-2 antibody or control IgG for Co-IP assays. Lysates were immunoprecipitated by using either polyclonal rabbit anti-Bcl-2 antibody or control IgG. Cell lysates and immunoprecipitates were examined by immunoblotting using anti-GFP antibody. The same membranes were also blotted with anti-Bcl-2 antibody (Santa Cruz) to determine IP specificity and efficiency. When GFP control vector was co-transfected with Bcl-2, GFP was not precipitated by anti-Bcl-2 antibody or control IgG, indicating that GFP did not interact with Bcl-2. However, when GFP-TR3/ΔDBD was transfected together with the Bcl-2 expression vector, a significant amount of GFP-TR3/ΔDBD was co-precipitated with Bcl-2 by anti-Bcl-2 antibody but not by control IgG. This Co-IP was specific because Bcl-2 co-transfection was necessary. Analysis of other TR3 mutants revealed that the C-terminal domain (DC3), but not the N-terminal domain (N168), of TR3/ΔDBD was responsible for binding Bcl-2. The C-terminal fragment DC1 (467-536 aa) strongly interacted with Bcl-2, while its deletion from TR3/ΔDBD (TR3/ΔDBD/ΔDC1) largely abolished the interaction. Furthermore, deletion of a putative amphipathic α-helix (471-488 aa) from TR3/ΔDBD (TR3/ΔDBD/A471-488) or mutation of Leu487, a critical amino acid reside for α-helix formation, to Ala (TR3/ΔDBD/L487A) significantly impaired the interaction between TR3/ΔDBD and Bcl-2. Thus, the DC1 region in the TR3 LBD is involved in the Bcl-2 interaction. In summary, it was found that the C-terminal domain (DC3), but not the N-terminal domain (N168), of TR3/ΔDBD was responsible for binding to Bcl-2.

DC-1 is a 69 residue fragment that corresponds to a portion of the ligand-binding domain (LBD) of the nuclear receptor family of proteins (Mages et al. 1994 *Mol Endocrinol* 8:1583-1591). LBDs are alpha-helical domains, composed of twelve alpha-helices that arrange themselves in complex helix bundles (Bourguet et al. 1995 *Nature* 375:377-382). The DC-1 segment of TR3 corresponds to helices 6-9 of LBDs (Mages et al., 1994, supra; Bourguet et al 1995, supra) indicating that about ⅔ of DC-1 is alpha helical.

The 69 amino acid C-terminal fragment (DC1) was able to strongly interact with Bcl-2, whereas deletion of DC1 from TR3/(DBD (TR3/(DBD/(DC1) largely abolished its interaction with Bcl-2. However, the interaction of DC1 with Bcl-2 was slightly weaker than that of DC3 and Bcl-2. Indeed, the C-terminal portion of DC3 (JK5) also exhibited slight interaction with Bcl-2.

To further determine the interaction of DC1 with Bcl-2, a region of hydrophobic amino acids (HRLGCARGFGDWID-SILA—SEQ ID NO: 1) was deleted from TR3/ΔDBD, and the resulting mutant (TR3/ΔDBD/A471-488) was analyzed for its interaction with Bcl-2. TR3/ΔDBD/A481-488, with eighteen amino acids from 471 to 488 in the DC1 region deleted from TR3/ΔDBD, TR3/ΔDBD/1483A (with Ile483 replaced with Ala) and TR3/ΔDBD/L487A (with Leu487 replaced with Ala) were analyzed for their interaction with Bcl-2 by in vivo Co-IP assay as described above. As compared to TR3/ΔDBD, the mutant showed only a very weak interaction with Bcl-2. Moreover, a single hydrophobic amino acid mutation (Ile 483 or Leu 487) largely abolished the interaction of TR3/ΔDBD and Bcl-2. These data further confirmed the role of DC1 in mediating the interaction between TR3 and Bcl-2.

Example 4

Characterization of TR3/Bcl-2 Interaction

Figure 3:
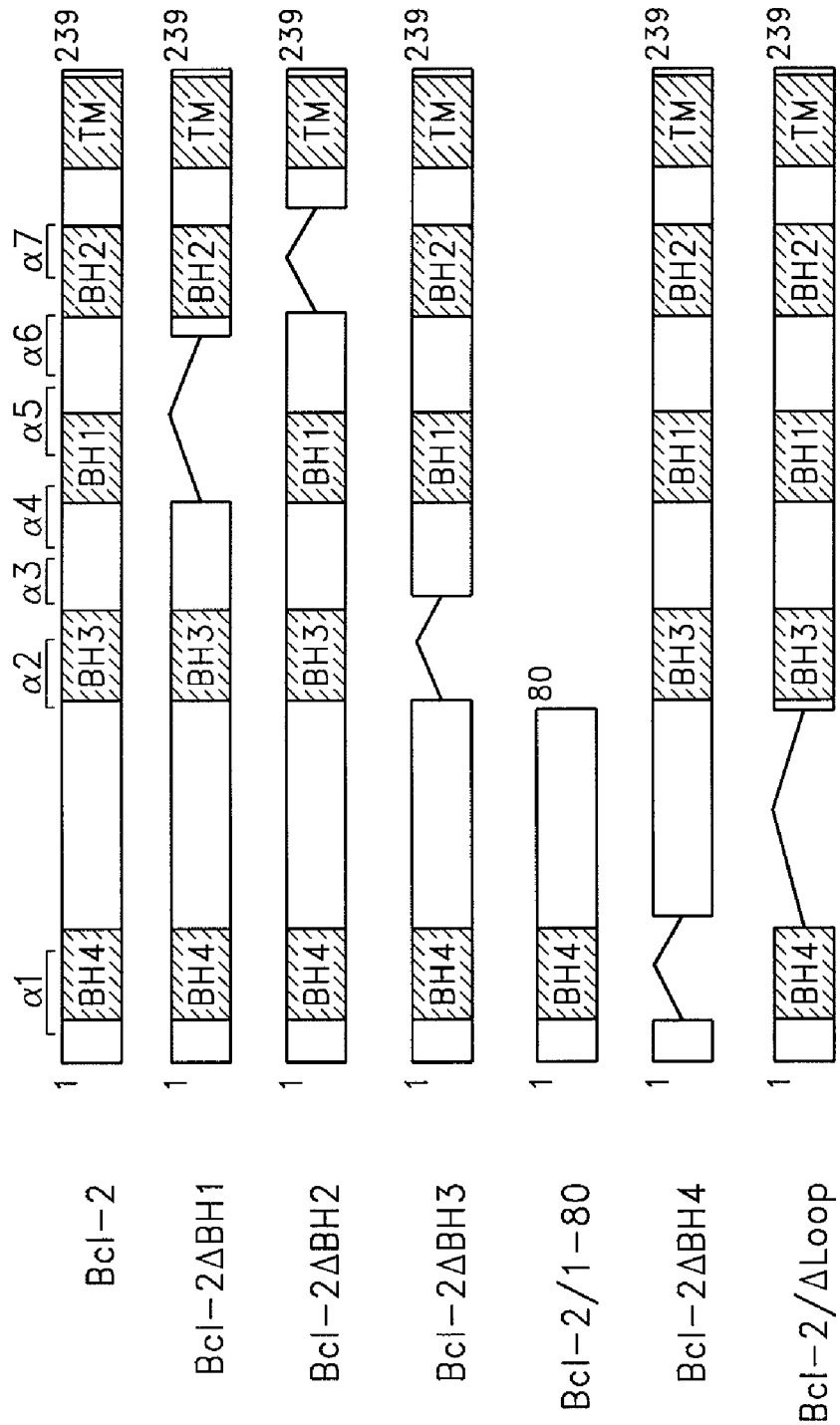
FIG. 3 is a schematic representation of Bcl-2 mutants with the Bcl-2 homology (BH) and loop domains and α-helical region indicated.

Binding of BH3 domain to Bcl-2 is mediated by a hydrophobic cleft formed by the BH1, BH2, and BH3 region of Bcl-2 (Sattler et al. 1997 *Science* 275:983-986). To determine whether TR3/ΔDBD bound to the Bcl-2 hydrophobic groove, several Bcl-2 mutants with mutations of amino acids, Tyr108, Leu137, or Arg146, critical for the formation of the hydrophobic cleft, were analyzed for their interaction with TR3/ΔDBD. A schematic representation of these mutants is shown in FIG. 3 with the Bcl-2 homology (BH) and loop domains and α-helical region indicated. These Bcl-2 mutants are defective in forming the hydrophobic groove. Mutations in the Bcl-2 hydrophobic groove abolish Bcl-2 interaction with Bax. The Bcl-2 mutants, Y108KBcl-2, L137ABcl-2 and R146QBcl-2, were analyzed for their interaction with GFP-TR3/ΔDBD in 293T cells by Co-IP assay as described in Example 2. Briefly lysates from HEK293T cells transfected with GFP-TR3/ΔDBD and the empty vector or the indicated Bcl-2 plasmid were used. GFP-TR3/ΔDBD (6 μg) was expressed in HEK293T cells with or without Bcl-2 (2 μg) in the presence or absence of Bax (2 μg). Lysates were immunoprecipitated with anti-Bcl-2 antibody. Immunoprecipitates and lysates were examined by Western blotting using the appropriate antibodies. The deletion or point mutations (Y108K, L137A, G145A or R146Q) in Bcl-2 abolished or reduced the interaction with Bax. In contrast, they were still capable of binding to TR3/ΔDBD. Thus, the hydrophobic cleft of Bcl-2 is not involved in the interaction with TR3, indicating that TR3 interacts with Bcl-2 in a manner that is different from other known Bcl-2-interacting proteins.

The ability of Bax or Bcl-Gs, a BH3-only Bcl-2-family protein, to compete with TR3 for binding Bcl-2 was also analyzed by immunoprecipitation. GFP-DC1 (4 μg) was expressed in HEK293T cells with or without Bcl-2 (2 μg) in the presence or absence of GFP-Bcl-Gs or GFP-Bcl-Gs/L216E (4 μg). Lysates were immunoprecipitated by anti-Bcl-2 antibody, followed by Western blotting with anti-GFP or anti-Bcl-2 antibodies. The results showed that neither Bcl-Gs nor Bax interfered with DC1 or TR3/ΔDBD binding to Bcl-2. Rather, these proteins consistently enhanced the interaction of Bcl-2 with the TR3 mutants. In contrast, Bcl-Gs containing a mutation in its BH3 region (Bcl-Gs/L216A), known to prevent binding to Bcl-$X_L$Bcl-2, did not enhance the interaction between DC1 and Bcl-2. These results demonstrate that TR3 binds Bcl-2 in a manner different from Bcl-Gs and Bax and that the BH3-binding hydrophobic groove in Bcl-2 is not required.

The above observation that deletion of the BH1, BH2, or BH3 domain from Bcl-2 had no effect on its interaction with TR3 suggested that the N-terminal portion of the protein was responsible for binding TR3. Therefore, TR3/ΔDBD was analyzed as to its interaction with a fragment of Bcl-2 comprising the first 80 amino acids (Bcl-2/1-80). Co-IP assays demonstrated that Bcl-2/1-80, like the full-length Bcl-2, strongly interacted with TR3/ΔDBD. The Bcl-2/1-80 fragment encompasses the N-terminal BH4 domain followed by an unstructured loop domain of approximately 50 amino acids length. To determine whether the BH4 domain or the loop region was responsible for binding to TR3/ΔDBD, TR3/ΔDBD interaction with Bcl-2 mutants lacking the BH4 domain (Bcl-2/ΔBH4) or the loop region (Bcl-2/ΔLoop) was analyzed. Co-IP assays demonstrated that the Bcl-2/ΔBH4 retained the ability to interact with TR3/ΔDBD, whereas Bcl-2/ΔLoop did not. Thus, the loop region of Bcl-2 is involved in binding to TR3.

Deletion of the loop region of Bcl-2 completely blocks paclitaxel-induced apoptosis (Rakesh et al. 1999 *PNAS USA* 96:3775-3780). To further investigate whether the loop region of Bcl-2 is responsible for its interaction with TR3/ΔDBD, TR3/ΔDBD was co-transfected with the first 80-residue fragment of Bcl-2 including the loop region and BH4 domain. The mutant strongly interacted with TR3/ΔDBD. Deletion of BH4 domain from Bcl-2 did not abolish the interaction, demonstrating that the loop region of Bcl-2 is responsible for binding to TR3/ΔDBD.

To further characterize the interaction between TR3 and Bcl-2, an experiment was performed to determine whether a BH3-only Bcl-2-family protein Bcl-Gs (Guo et al. 2001 *J Biol Chem* 276:2780-2785) could affect the binding of TR3 to Bcl-2. Bcl-2 was co-transfected into 293T cells with either GFP-DC1 or GFP-Bcl-Gs or a Bcl-Gs mutant and the co-immunoprecipitation (co-IP) was performed as described above. Bcl-Gs is known to bind to the hydrophobic cleft of Bcl-2. Interestingly, incubation of Bcl-Gs did not compete with DC1 for binding Bcl-2. Surprisingly, it enhanced the binding of DC1 to Bcl-2. The enhancing effect required its binding to Bcl-2 since mutant Bcl-Gs (L216EBcl-Gs) with a mutation in its BH3 domain, which abolishes its ability of binding Bcl-2, failed to enhance DC1 binding to Bcl-2. The observation that Bcl-G enhanced the interaction between DC-1 and Bcl-2 implies that Bcl-G and DC-1 bind different sites on Bcl-2. Similar results were obtained when BAX was analyzed. Thus, TR3 interacts with Bcl-2 in a manner that is different from that of Bcl-2-family proteins.

Both LBDs and Bcl-2-family proteins are characterized by plasticity; that is, they undergo conformational reorganization of helices upon either binding ligand (LBDs) (Bourguet et al. 1995, supra) or a variety of proteins including Bcl-2-family members (Bcl-2) (Sattler et al. 1997, supra). Bcl-2-family proteins form heterodimers with other family members including Bcl-2 when the alpha-helical BH3 domain of one member undergoes reorganization to bind the BH3 binding pocket of a second member (Sattler et al. 1997, supra). Bcl-G very likely interacts with Bcl-2 in this manner to enhance binding of DC-1. Many proteins interact with Bcl-2 possibly through helix-helix interactions. For example, the BAG-1 domain, which is a triple helix bundle, binds Bcl-2 (Brinknarova et al. 2001 *Nat Struct Biol* 8:349-352; Reed 1997 *Nature* 387:773-776). Thus, it is believed that one or more DC-1 helix or helices interact with Bcl-2 helices to induce a proapoptotic complex.

Example 5

Bcl-2 Mediates TR3 Mitochondrial Localization

Experiments were performed to determine whether Bcl-2 mediates TR3 mitochondrial targeting, including confocal microscopy, subcellular fractionation and RNA inhibition.

A. confocal microscopy—First an experiment was performed to determine whether the deletion mutant TR3/ΔDBD targets mitochondria via its interaction with Bcl-2. In confocal microscopy analysis, GFP-TR3/ΔDBD and Bcl-2 were transfected into 293T cells alone or together. Cells were then immunostained with anti-Bcl-2 antibody followed by Cy3-conjugated secondary antibody (Sigma) to detect Bcl-2, or with anti-Hsp60 antibody followed by Cy5-conjugated secondary antibody (Sigma) to detect mitochondria. Bcl-2, TR3/ΔDBD and mitochondria (Hsp60) were visualized using confocal microscopy and the three images were overlaid. TR3/ΔDBD expressed in 293T cells exhibited a diffuse distribution pattern. However, Bcl-2 colocalized with TR3/ΔDBD when they were coexpressed, displaying a distribution pattern overlaid extensively with that of Hsp60. Mutants of TR3 (TR3/ΔDBD/L487A and TR3/ΔDBD/A471-488) which did not bind Bcl-2 failed to colocalize with mitochondria.

B. Subcellular Fractionation—To examine the role of Bcl-2 in mitochondrial targeting of TR3 by an independent method, mitochondrial localization was also demonstrated by immunoblotting of the mitochondria-enriched heavy membrane (HM) fractions. The accumulation of Bcl-2-binding TR3/ΔDBD and non-binding TR3/ΔDBD/A471-488 was compared in mitochondria-enriched heavy membrane fractions of HEK293T cells transfected with or without Bcl-2. The purity of HM preparations was established by assessing the expression of mitochondrial Hsp60, nuclear protein PARP, and cytosolic/nuclear protein Jun N-terminal kinase (NJK). The heavy membrane fractions were prepared and analyzed for accumulation of TR3/(DBD by Western blotting using anti-GFP antibody. GFP-TR3/ΔDBD or GFP-TR3/ΔDBD/(471-488 (6 mg) and Bcl-2 (2 mg) expression vectors were transfected into HEK293T cells alone or together. HM fractions were prepared and analyzed for accumulation of TR3/ΔDBD in mitochondria by immunoblotting using anti-GFP antibody. The same membrane was also blotted with anti-Bcl-2, anti-Hsp60, anti-PARP, or anti-JNK antibody to ensure HM purity. whole lysate was prepared from cells transfected with TR3/ΔDBD and Bcl-2. TR3/ΔDBD accumulated in the HM fraction (in mitochondria) in the presence of Bcl-2. In contrast, TR3/ΔDBD/A471-488 was not found in the HM fraction, either in the absence or presence of Bcl-2, a result consistent with the confocal microscopy results above. These results demonstrate that Bcl-2 acts as a receptor for TR3 to target mitochondria.

C. Small interfering RNA (siRNA)—To complement these gene transfection experiments, a small interfering (si)RNA approach was used to determine the effect of suppressing endogenous Bcl-2 expression on TR3 mitochondrial targeting. Briefly, MGC80-3 cells were transfected with Bcl-2 siRNA SMARTPOOL® or control GFP siRNA or left alone. After 48 h, lysates were prepared and assayed by immunoblotting using anti-Bcl-2 and anti-β-actin antibodies. In MGC80-3 gastric cancer cells, a tumor cell line in which TR3 was reported to target mitochondria in response to specific apoptotic stimuli, Bcl-2 expression was almost completely inhibited by Bcl-2-specific siRNA, but not by GFP siRNA control. Both confocal microscopy and immunoblotting of HM fractions revealed that endogenous TR3 targeted mitochondria in MGC80-3 cells treated with 3-Cl-AHPC. However, transfection of Bcl-2 siRNA, but not control GFP siRNA, largely abolished mitochondrial targeting of TR3. 3-Cl-AHPC still induced expression of TR3 and translocation of TR3 from the nucleus to cytosol, but TR3 failed to target mitochondria in the absence of Bcl-2. Similarly, inhibition of endogenous Bcl-2 expression by Bcl-2 antisense oligonucleotides impaired TR3 mitochondrial targeting in H460 lung cancer cells.

The next approach involved using a fragment of Bcl-2 consisting of the TR3 interaction domain (loop region) to identify whether it could act in a dominant-negative fashion to inhibit TR3 mitochondrial targeting in LNCaP cells. Cells transiently transfected with the GFP-Bcl-2/1-90 mutant comprising of the first 90 N-terminal amino acids were treated with TPA to induce expression of TR3 and mitochondrial targeting of the endogenous TR3. In cells transfected with GFP-Bcl-2/1-90, TR3 failed to target mitochondria, displaying a diffuse cytosolic distribution pattern in contrast to non-transfected cells in the same culture dish. Thus, Bcl-2/1-90 inhibits TR3 mitochondrial targeting, probably by competing with endogenous Bcl-2 for binding to TR3. Together, these results demonstrate that Bcl-2 acts as a receptor for TR3, and is responsible for its mitochondrial targeting.

Example 6

Bcl-2 Mediates TR3-Induced Cytochrome c Release

The involvement of TR3/Bcl-2 interaction in TR3-induced cytochrome c release was also studied. GFP-TR3/ΔDBD (4 μg) and Bcl-2 (2 μg) were transfected into 293T cells alone or together. GFP-TR3/ΔDBD were also co-expressed with Bcl-2/ΔTM or Bcl-2/Y108K (2 μg). Cells were immunostained with anti-cytochrome c (cyt c) or anti-Bcl-2 antibody followed by Cy5 conjugated secondary antibody (Sigma) to detect cytochrome c, or with anti-Hsp60 followed by Cy3-conjugated secondary antibody (Sigma) to detect mitochondria or anti-Bcl-2 antibody followed by Cy5-conjugated secondary antibody to detect Bcl-2. Cytochrome c, TR3/(DBD, and mitochondria (Hsp60) were visualized using confocal microscopy, and images for TR3/(DBD and Hsp60 were overlaid. Approximately 75% of the TR3/ΔDBD and Bcl-2 colocalized cells displayed various levels of diffuse cyt c staining. In the absence of Bcl-2 cotransfection, TR3/ΔDBD expression did not cause any release of cytochrome c from mitochondria as determined by confocal microscopy analysis, which showed punctate cytochrome c staining. Nor did transient expression of Bcl-2 alone. However, cotransfection of Bcl-2 and TR3/ΔDBD, resulted in colocalization of TR3/ΔDBD and Bcl-2 and significant release of cytochrome c from mitochondria. Cyt c release involved mitochondrial localization of TR3/ΔDBD and Bcl-2, because it did not occur upon co-transfection of TR3/ΔDBD with Bcl-2/ΔTM, a Bcl-2 mutant lacking the ability to target mitochondria. Interestingly, co-expression of TR3/ΔDBD and Bcl-2/Y108K did not induce cyt c release, although they colocalized. This result suggests that the interaction between TR3/ΔDBD and Bcl-2 is insufficient for inducing cyt c release.

TR3/ΔDBD targets mitochondria in NCI-H460 cells, which express high levels of Bcl-2 (Lu et al. 2001 Cancer Chemother Pharmacol 47:170-178). To determine whether Bcl-2 is involved in mitochondrial targeting of TR3, GFP-TR3/ΔDBD was transfected into Calu-6 lung cancer cells, which express low levels of Bcl-2. GFP-TR3/ΔDBD and Bcl-2 were transfected into Calu-6 lung cancer cells alone or together. Cells were then immunostained with anti-Bcl-2 antibody followed by Cy3-conjugated secondary antibody to detect Bcl-2, or with anti-Hsp60 antibody followed by Cy5-conjugated secondary antibody to detect mitochondria. Bcl-2, TR3/(DBD and mitochondria (Hsp60) were visualized using confocal microscopy. Unlike its exclusive localization in mitochondria in NCI-H460 cells, TR3/ΔDBD was diffusely distributed in Calu-6 cells, but targeted mitochondria when Bcl-2 was co-transfected. Moreover, cytochrome c was released from mitochondria of TR3/ΔDBD-Bcl-2 cotransfected Calu-6 cells. Thus, Bcl-2 is involved in TR3/ΔDBD to targeting of mitochondria and the subsequent induction of cytochrome c release.

Example 7

Effect of Various TR3 Mutants on Apoptotic Potential of Bcl-2

Figures 4A, 4B, 4C:
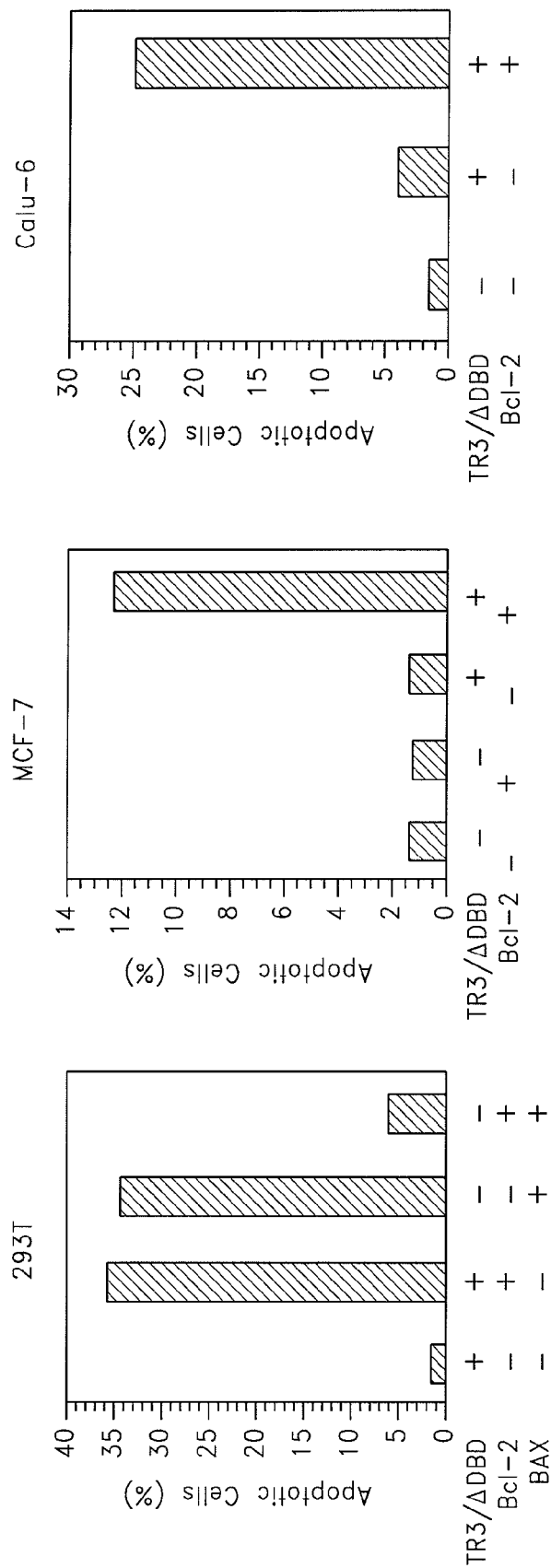
FIGS. 4 *a-c* are graphs showing that expression of both TR3/ΔDBD and Bcl-2 results in apoptosis of lung cancer and breast cancer cells.
Figure 5:
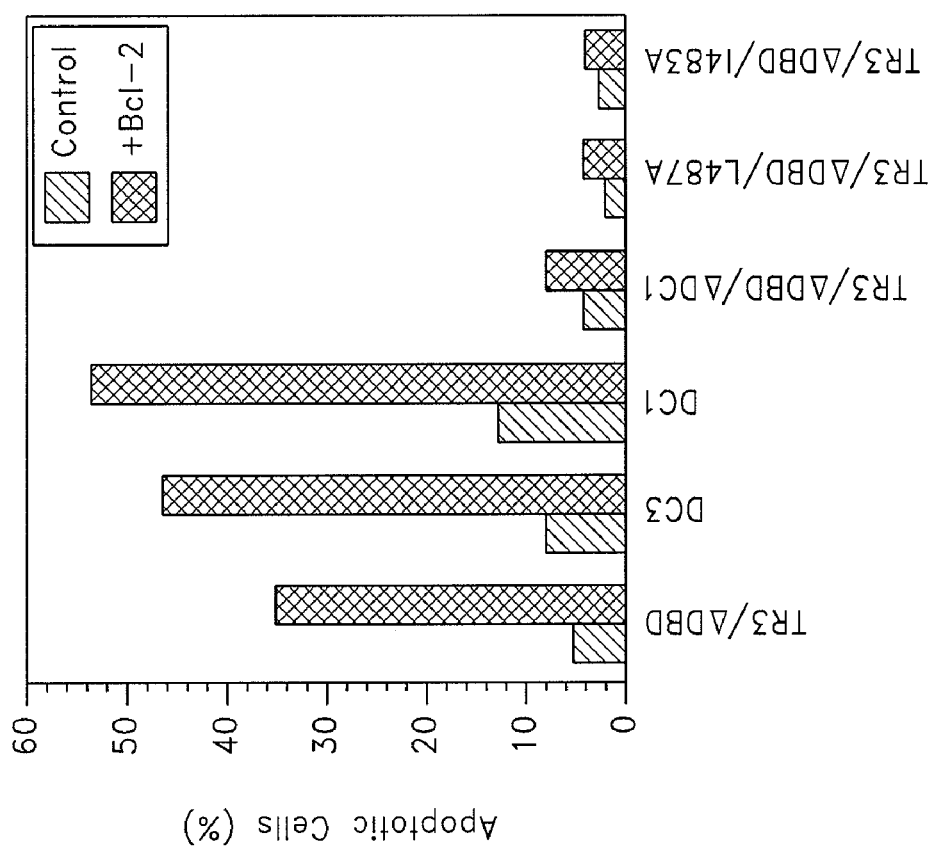
FIG. 5 is a graph showing the effect of TR3 mutants on apoptotic potential of Bcl-2.

DAPI staining was used to study the apoptotic effect of TR3/Bcl-2 interaction. 293T cells were transfected with GFP-TR3/ΔDBD alone or together with Bcl-2. After 36 h, nuclei were stained by DAPI and nuclear fragmentation and chromatin condensation were identified. Cells were also stained with anti-Bcl-2 antibody, followed by TRITC-conjugated secondary antibody (Sigma). Bcl-2 and GFP-ΔDBD expression and nuclear morphology were visualized by fluorescence microscopy, and the two images were overlaid. Transfected TR3/ΔDBD did not cause any nuclear fragmentation or condensation in 293T cells. But, when Bcl-2 was cotransfected, a significant amount of transfected cells underwent apoptosis. For example, approximately 4% of cells transfected with either TR3/ΔDBD or Bcl-2 were apoptotic, compared to 35% of cell transfected with both. The pro-apoptotic effect of Bcl-2 seen upon co-expression, was specific to TR3, because Bax-induced apoptosis was effectively prevented by Bcl-2 co-expression. Cotransfection of Bcl-2, however, prevented BAX-induced apoptosis in these cells (see FIG. 4). The effect of Bcl-2 on apoptotic potential of TR3/ΔDBD in lung cancer and breast cancer cells was also investigated. In these experiments, Bcl-2 was cotransfected into the 293T, MCF-7, or Calu-6 cell lines with or without TR3 (DBD or BAX. After 36 h, nuclei were stained by DAPI. Cells displaying nuclear condensation or fragmentation were scored. In the absence of Bcl-2, expression of TR3/ΔDBD did not show any apoptotic effect in MCF-7 breast cancer and Calu-6 lung cancer cells. However, co-expression of Bcl-2 resulted in strong induction of apoptosis in both cell lines. Thus, the TR3-Bcl-2 interaction is involved in the induction of cytochrome c release and apoptosis.

The effect of inhibiting endogenous Bcl-2 expression on the TR3-dependent apoptosis in MGC80-3 cells was next analyzed. Treatment of control GFP-siRNA-transfected cells with 3-Cl-AHPC resulted in apoptosis, consistent with prior studies showing that this agent induces TR3 expression and mitochondrial targeting. However, 3-Cl-AHPC-induced apoptosis was suppressed by more than half (about 60%) in Bcl-2 siRNA-transfected cells. Similar results were obtained in H460 lung cancer cells. Moreover, expression of the Bcl-2/1-90 protein, which inhibited TR3 mitochondrial targeting, also suppressed TR3-dependent apoptosis induced by apoptotic stimuli, such as TPA and 3-Cl-AHPC, in LNCaP cells. Thus, Bcl-2 can manifest a pro-apoptotic phenotype in settings where TR3 is expressed and targets to mitochondria.

To extend some of these studies using established tumor cell lines to normal cells, experiments were performed using primary cultures of peripheral blood lymphocytes (PBLs). TR3 subcellular localization was studied by both confocal microscopy and subcellular fractionation approaches. For microscopy experiments, freshly isolated PBLs were transfected with GFP-TR3, then treated with phorbol ester TPA and the calcium ionophore ionomycin, which induce TR3-dependent apoptosis of T-lymphocytes. Without treatment, GFP-TR3 mainly resided in the nucleus. After treatment, GFP-TR3 was found in the cytoplasm, colocalizing with cotransfected DsRed2-Mito, a red fluorescent protein (RFP) fused with a mitochondria-targeting sequence. Subcellular fractionation experiments revealed that TPA/ionomycin treatment induced accumulation of endogenous TR3 in HM fractions. Interestingly, this treatment also altered the migration of TR3 protein, suggesting a possible post-translational modification. Thus, both transfected and endogenous TR3 also targets to mitochondria in primary lymphocytes.

The role of Bcl-2 in TR3-dependent apoptosis in PBLs was also studied. Treatment with TPA/ionomycin induced extensive apoptosis of PBLs, which was partially inhibited by transfecting Bcl-2 anti sense oligonucleotides or TR3 siRNA. The role of Bcl-2 in TR3/ΔDBD targeting to mitochondria and in TR3/ΔDBD-induced apoptosis in PBLs was studied in transfection experiments. In these experiments, GFP-TR3/ΔDBD colocalized extensively with DsRed2-Mito and potently induced PBL apoptosis, as determined by annexin V-staining. In contrast, TR3/ΔDBD-induced apoptosis was considerably suppressed by Bcl-2 antisense oligonucleotides in PBLs. Thus, endogenous Bcl-2 contributes to TR3-dependent apoptosis in primary lymphocytes.

Example 8

Domains in TR3 and Bcl-2 Involved in their Apoptotic Activity

To characterize the pro-apoptotic mechanism of Bcl-2 in the setting of TR3-induced apoptosis, various TR3 mutants and Bcl-2 mutants were co-expressed in HEK293T cells. TR3 mutants were transfected into 293T cells together with or without Bcl-2 expression vector or with Bcl-2 mutants. After 36 h, nuclei were stained by DAPI. Cells displaying nuclear condensation or fragmentation were scored. Expression of DC3 and DC1 that showed strong interaction with Bcl-2 potently induced apoptosis of 293T cells, when Bcl-2 was co-expressed (see FIG. 18). In contrast, coexpression of TR3/ΔDBD/ΔDC1 that failed to interact with Bcl-2 did not result in apoptosis of 293T cells, indicating that the DC1 region is capable of inducing apoptosis. DC3 also induced apoptosis, consistent with the ability of these TR3 fragments to bind Bcl-2. The role of the DC1 in inducing the apoptotic potential of Bcl-2 was also demonstrated by the observation that coexpression of either TR3/ΔDBD/ΔDC1, TR3/ΔDBD/A471-488, TR3/ΔDBD/L487A or TR3/ΔDBD/1483A and Bcl-2 failed to confer the apoptotic potential of Bcl-2.

Figure 6:
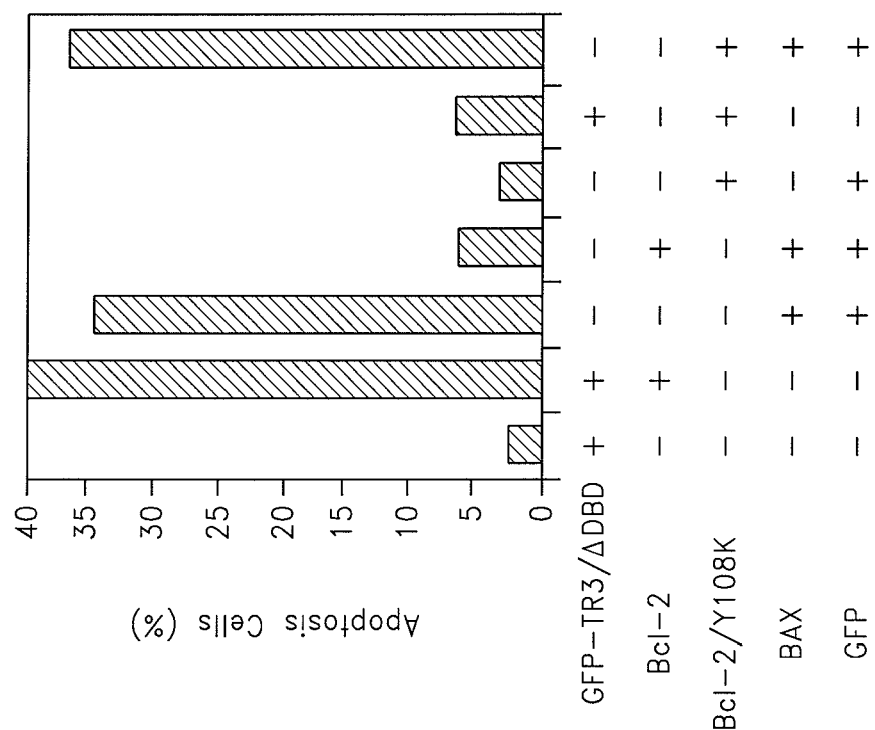
FIG. 6 is a graph showing that the BH3 domain is involved in TR3/ΔDBD-induced apoptosis.

The role of various Bcl-2 mutants in mediating apoptosis induction by TR3 was next studied. Bcl-2 effectively suppressed apoptosis induced by Bax expression in HEK293T cells, indicating that Bcl-2 is a potent anti-apoptotic molecule with respect to Bax-induced apoptosis. The hydrophobic cleft of Bcl-2 is involved in its anti-apoptotic effect through its interaction with BH3 domain of pro-apoptotic molecules (Reed 1997 Semin Hematol 34:9-19; Reed 1997 Nature 387: 773-776). To investigate whether the BH3 domain-binding motif of Bcl-2 is also involved in its apoptotic effect, various Bcl-2 mutants including Y108K Bcl-2, with a mutation in the BH3 domain-binding cleft, L137A, and G145A (all with impaired interaction with bax), were cotransfected together with TR3/ΔDBD. More specifically, expression vectors for Bcl-2 or BH3 domain point mutant of Bcl-2 or other mutants were co-transfected together with or without TR3/ΔDBD or BAX or GFP into 293T cells, and after 36 hours, nuclei were stained by DAPI and the percentage of GFP-positive cells with nuclear condensation or fragmentation was scored (FIG. 6). Y108K Bcl-2 could not bind to BAX and failed to prevent BAX-induced apoptosis in 293T cells (FIG. 6). Bcl-2 mutations (Y108K, L137A, G145A) that impaired its interaction with Bax, abolished the Bcl-2 inhibitory effect on Bax-induced apoptosis, consistent with previous observations that the hydrophobic cleft of Bcl-2 is essential for its anti-apoptotic effect. Interestingly, Y108K was unable to induce apoptosis when it was cotransfected with TR3/ΔDBD, although it is capable of binding to TR3/ΔDBD. Thus, an intact BH3 domain-binding motif in Bcl-2 is involved in its pro-apoptotic effect. In contrast to the inhibitory effect of Bcl-2 on Bax-induced apoptosis TR3/ΔDBD-induced apoptosis was augmented by co-expression of Bcl-2 in HEK293T cells. As expected, co-expression of TR3/ΔDBD with Bcl-2/ΔLoop did not induce cell death, consistent with the inability of this Bcl-2 mutant to bind TR3.

Mitochondrial targeting of TR3 has been previously identified as being involved in its apoptotic effect. To study whether mitochondrial localization of the TR3/ΔDBD/Bcl-2 complex was involved in their apoptotic effect, TR3/ΔDBD was cotransfected with Bcl-2/ΔTM, a Bcl-2 lacking its transmembrane domain. Coexpression of TR3/ΔDBD and Bcl-2/ΔTM did not result in apoptosis of 293T cells. Thus, mitochondrial localization of TR3/ΔDBD/Bcl-2 complex is involved in this apoptotic effect.

Experiments to delineate the structure-function relations involved in the pro-apoptotic effect of Bcl-2 in the context of TR3-induced apoptosis showed the following: Though capable of binding TR3/ΔDBD, mutants of Bcl-2 lacking the membrane-anchoring TM domain, the BH1 domain, BH2 domain, or BH3 domain were incapable of inducing apoptosis when co-expressed with TR3/ΔDBD. Similarly, a BH3 mutant of Bcl-2 (Y108K) also failed to induce apoptosis in collaboration with TR3, though it retained the ability to bind TR3. This observation is consistent with the data above, showing that Bcl-2/Y108K failed to induce cyt c release when co-expressed with TR3/ΔDBD. Moreover, mutations of the BH3-binding pocket of Bcl-2, L137A and G145A, which abrogated the ability of Bcl-2 to suppress apoptosis induced by Bax, retained the ability to promote apoptosis when co-expressed with TR3/ΔDBD. Thus, an intact hydrophobic groove in Bcl-2 is involved in its anti-apoptotic activity but not its pro-apoptotic activity, demonstrating a structural distinction between these two opposing phenotypes of Bcl-2.

Example 9

Mitochondrial Targeting of TR3 in Neurons

To further investigate TR3 targeting of mitochondria, rat primary neurons were treated with the dopaminergic neurotoxin 1-methyl-4-phenyl-1,2,3,6-tetrahydropyridine (MPTP). MPTP induces Parkinson's disease in animals. Rat primary dopaminergic neurons were treated with or without 100 μM MPTP for one (1) hour, then immunostained with anti-TR3 antibody followed by Cy3-conjugated secondary antibody (Geneka) to detect endogenous TR3, or with anti-Hsp60 antibody followed by Cy5-conjugated secondary antibody (Sigma) to detect mitochondria. Neurons were identified by staining with neuron marker. TR3 and mitochondria (Hsp60) were visualized using confocal microscopy. Endogenous TR3 was found exclusively in the cytoplasm and colocalized with mitochondria in MPTP-treated neurons. TR3 was found only in the nucleus of non-treated neurons. Thus, TR3 mitochondrial localization plays a role in mediating the effect of dopaminergic neurotoxin in neurons.

The effect of phorbol ester (TPA) and calcium ionophore (A23187) on TR3 subcellular localization in primary hippocampal neurons was also examined. Rat primary hippocampal neurons were treated with or without 100 ng/ml TPA and 10 μM A23187 for 1 hour. The neurons were then immunostained with anti-TR3 antibody (Geneka) followed by Cy3-conjugated secondary antibody (Geneka) to detect endogenous TR3, or with anti-Hsp60 antibody followed by Cy5-conjugated secondary antibody (Sigma) to detect mitochondria. TR3 and mitochondria (Hsp60) were visualized using confocal microscopy. Treatment with TPA and A23187 caused TR3 relocalization from the nucleus to the mitochondria. Thus, TR3 mitochondrial localization is associated with neuronal death.

To determine whether additional molecules could induce apoptosis in a manner similar to that resulting from the interaction between TR3 and Bcl-2, another member of the Bcl-2-family, the apoptosis antagonist Bcl-$X_L$, was studied, as described below.

Example 10

TCTP Binds Bcl-$X_L$ and Induces Apoptosis

Bcl-$X_L$ cDNA was constructed into the pGilda yeast two-hybrid vector. Using pGilda-Bcl-$X_L$ as bait, a human testis cDNA library was used in yeast two-hybrid screening to screen for potential Bcl-$X_L$ interacting proteins. pGilda-Bcl-$X_L$ and a reporter plasmid pSH18-34 were co-transfected into EGY48 yeast cells. The transfectant yeast cells were then transfected in large scale with yeast two-hybrid library cDNA plasmids. Positive clones were identified through selection in Leucine-deficient media. A total of 95 positive colonies were identified. These positive clones were further examined for a second reporter expression by β-gal filter assays. Among these clones, 29 of them tested positive. These clones were further examined by mating assays to confirm the interaction with Bcl-$X_L$. Ten positive clones were isolated and sequenced to reveal their identity. Two of them encode cDNAs identical to human Translationally-Controlled Tumor Protein (TCTP).

TCTP is a calcium-binding protein with no previous identified role in apoptosis regulation. It has been discovered that TCTP interacts with Bcl-$X_L$. HEK293T cells were transfected with pcDNA3-HA vector containing Bcl-$X_L$ together with GFP or GFP-TCTP. Cell lysates were immunoprecipitated with polyclonal anti-GFP antibody. The immunoprecipitates or the lysates were blotted with anti-HA or anti-GFP antibodies, respectively.

Fluorescence microscopy demonstrated the co-localization of these proteins. GFP, RFP, GFP-TCTP and RFP-Bcl-$X_L$ plasmids were transfected into cos-7 cells. Images were photographed with a confocal microscope. Furthermore, Bcl-$X_L$ recruits TCTP from cytosolic location to the mitochondria.

Figure 7:
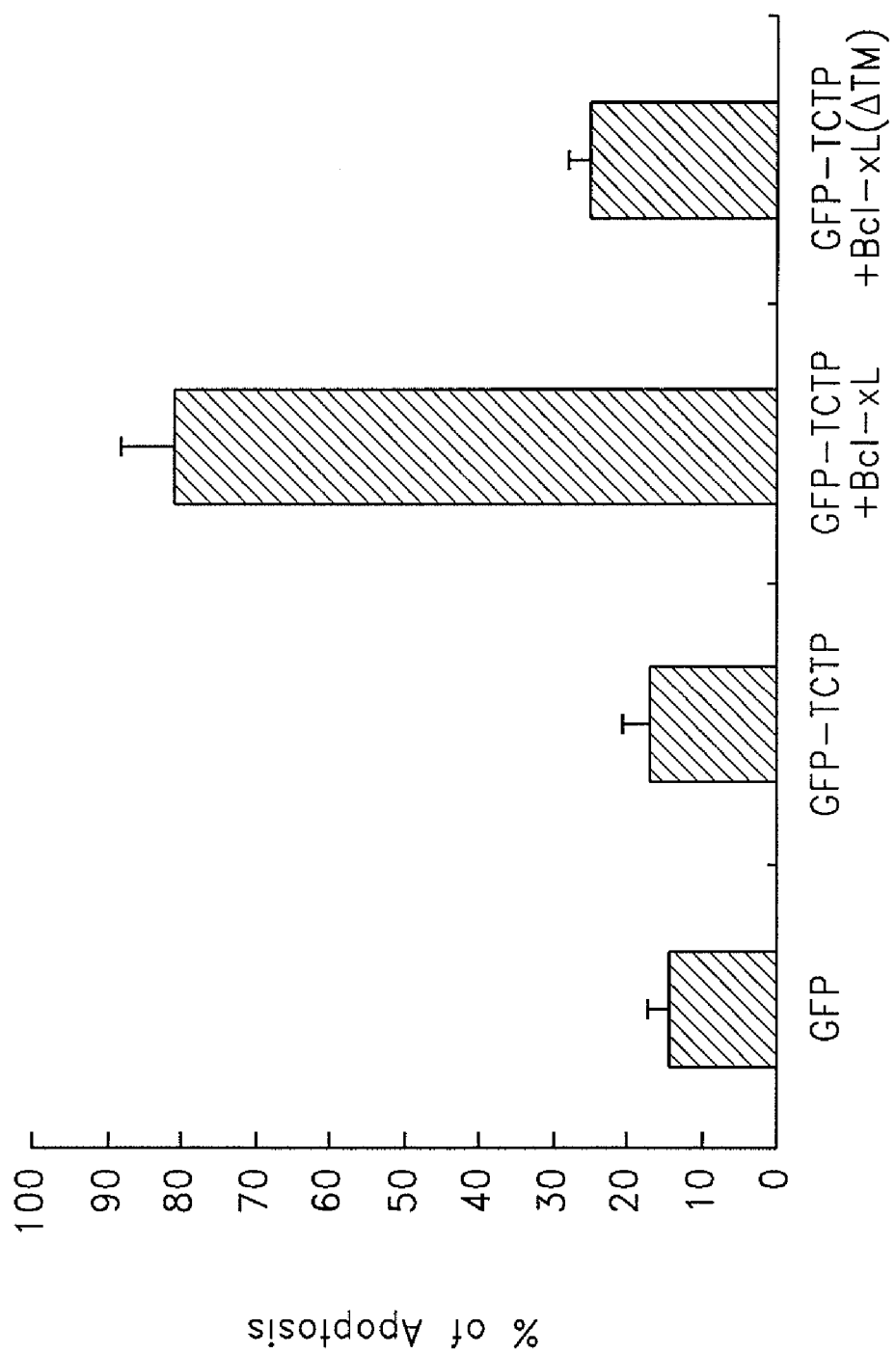
FIG. 7 is a graph illustrating apoptosis in Bcl-$X_L$ overexpressing cells induced by TCTP.

An interesting and unique functional property of TCTP, however, is that it not only induces apoptosis when overexpressed in cells, similar to many pro-apoptotic proteins, it also kills cells better when Bcl-$X_L$ is co-expressed with it. GFP or GFP-TCTP plasmids were co-transfected with RFP-Bcl-$X_L$ or RFP-Bcl-$X_L$ (ΔTM) plasmids into cos-7 cells. Cells were fixed and stained with DAPI 48 hours after transfection (n≧200 total cells evaluated) and the percentage of apoptotic cells was calculated (mean±SD, n=3) (FIG. 7). More apoptosis of MCF7 cells was observed when TCTP was expressed together with Bcl-$X_L$ than without Bcl-$X_L$. This indicates that TCTP's interaction with Bcl-$X_L$ converts Bcl-$X_L$ from an anti-apoptotic to a pro-apoptotic protein.

Figure 8:
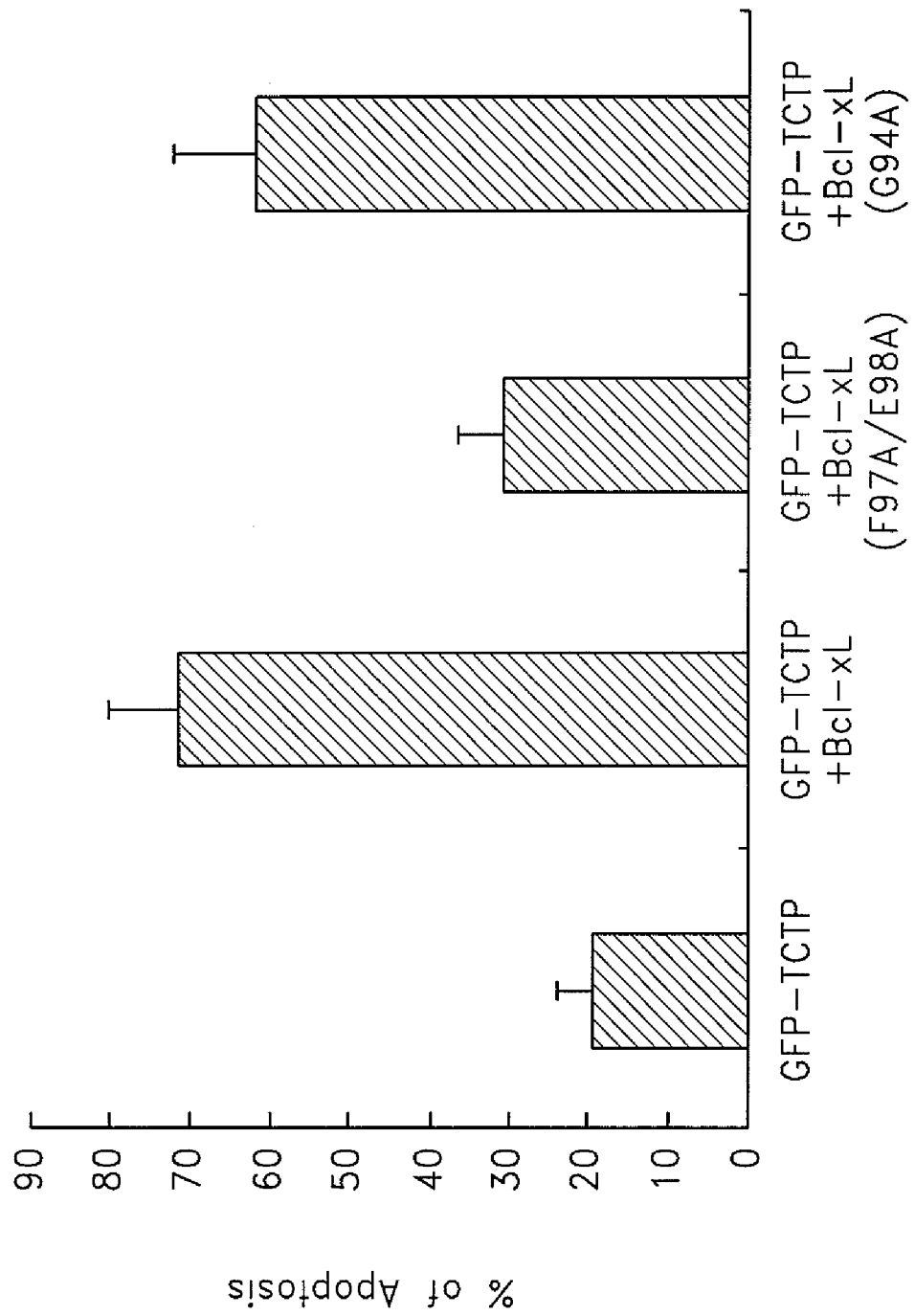
FIG. 8 is a graph that illustrates that the BH3 domain of Bcl-$X_L$ is involved in TCTP induced apoptosis.

Additionally, it was shown that the BH3 domain of Bcl-$X_L$ was involved in the TCTP induced apoptosis. GFP-TCTP plasmids were co-transfected with RFP-Bcl-$X_L$, RFP-Bcl-$X_L$ (F97A/E98A) or RFP-Bcl-$X_L$ (G94A) plasmids into cos-7 cells. Cells were fixed and stained with DAPI 48 hours after transfection (n≧200 total cells evaluated) and the percentage of apoptotic cells was calculated (mean±SD, n=3). Results are shown in FIG. 8.

Example 11

Bcl-2 Undergoes a Conformational Change Upon TR3 Binding

Pro-apoptotic Bcl-2-family proteins Bax and Bak have been shown to undergo conformational changes in association with their conversion from latent to active killer proteins. Therefore the possibility that a conformational change might be involved in the conversion of Bcl-2 from anti-apoptotic to pro-apoptotic function was explored. To this end, the effects of TR3 on binding of Bcl-2 to various anti-Bcl-2 antibodies recognizing different epitopes were compared. Antibody binding to Bcl-2 was measured by immunofluorescence using flow cytometry (See FIGS. 9*a-f*) or by immunoprecipitation.

First, HEK293T cells were transfected with Bcl-2 (5 μg), together with GFP-TR3/ΔDBD or the control GFP vector (5 μg) for 14 h., and immunostaining was performed on fixed and permeabilized cells using rabbit polyclonal antibody raised against the whole Bcl-2 protein, mouse monoclonal antibody directed against the Bcl-2 BH3-binding pocket, or polyclonal antibody raised against the Bcl-2 BH3 domain followed by SRPD-conjugated secondary antibody (Southern Biotech). The transfected cells were identified by their green fluorescence by flow cytometric analysis, and the intensity of Bcl-2 immunofluorescence was compared between the GFP-positive and GFP-negative cells. Bcl-2 immunofluorescence was undetectable in control GFP-expressing cells by staining with the antibody directed against the Bcl-2 BH3 Domain but dramatically increased in GFP-TR3/ΔDBD-expressing cells (FIGS. 9*a* and 9*d*), suggesting increased availability of this epitope in Bcl-2 upon TR3/ΔDBD co-expression. In contrast, the immunofluorescence obtained by staining with the antibody directed against the BH3-binding pocket was reduced by co-expression of GFP-TR3/ΔDBD, suggesting decreased availability of this epitope (FIGS. 9*b* and 9*e*). These alterations in binding of epitope-specific antibodies to Bcl-2 in response to GFP-TR3/ΔDBD co-expression were not due to changes in Bcl-2 levels, because GFP-TR3/ΔDBD co-expression did not result in altered Bcl-2 immunofluorescence when the Bcl-2 antibody raised against the whole protein was used. In addition, immunoblotting analysis and BD cytometric bead assays revealed equivalent levels of Bcl-2 protein in the presence of GFP or GFP-TR3/ΔDBD. Also, TR3/ΔDBD co-expression did not modify binding of these epitope-specific antibodies to Bcl-2/ΔLoop, as determined by immunofluorescence measurements using flow cytometry. This TR3/ΔDBD-induced change in Bcl-2 conformation was also observed in PBLs in addition to HEK293T cells (See FIGS. 9*a-f*).

Second, the effects of TR3/ΔDBD on Bcl-2 conformation were studied by immunoprecipitation assays. These experiments showed that co-expression of TR3/ΔDBD reduced binding of Bcl-2 by the antibody directed against the BH3-binding pocket, while enhancing binding of Bcl-2 by the antibody directed against the BH3 domain. In contrast, TR3Δ/DBD did not affect the immunoprecipitation efficiency of the Bcl-2 antibody raised against the whole protein. Together, these results demonstrated that TR3 binding induced a conformational change, resulting in exposure of its BH3 domain.

Pro-apoptotic BH3-only members of the Bcl-2 family induce apoptosis by binding to other Bcl-2 family members through their BH3 domains. Therefore, it was of interest to determine whether TR3 binding alters the ability of Bcl-2 to bind Bcl-$X_L$ or Bak, as measured by Co-IP assays. At least when assessed in detergent-containing lysates of cells by Co-IP, Bcl-2 bound Bcl-$X_L$ and Bak independently of TR3. To address the possibility that Bcl-2 bound differently to Bcl-$X_L$ and Bak in the presence of TR3/ΔDBD, two Bcl-2 mutants were analyzed. Bcl-2/L137A, a BH3-binding pocket mutant that retained killing activity in the presence of TR3/ΔDBD, interacted with Bcl-$X_L$ and Bak only when TR3/ΔDBD was co-expressed. In contrast, binding to Bcl-$X_L$ and Bak of the Bcl-2/Y108K B3 domain mutant was not modulated by co-expression of TR3. Thus, TR3 binding may result in altered association of Bcl-2 with other members of the Bcl-2 family. Moreover, the observation that Bcl-2/L137A, but not Bcl-2/Y108K, was capable of killing cells in collaboration with TR3/ΔDBD suggested that exposure of the BH3 domain of Bcl-2 may be responsible for the conversion of Bcl-2 to a pro-apoptotic molecule.

The above data suggested that Bcl-2, upon TR3 binding, induces apoptosis through its BH3 domain. BH3-only proteins exert their apoptotic effects through either Bax or Bak. The involvement of Bax and Bak in Bcl-2-dependent apoptosis induced by TR3 was therefore examined. Co-transfection of TR3/ΔDBD and Bcl-2 resulted in a similar degree of apoptosis in HCT116 cells and HCT116 cells lacking Bax (HCT 116 Bax$^{-/-}$), suggesting that expression of Bax was not crucial. This was also supported by the observation that H460 cells, which underwent extensive apoptosis in response to 3-Cl-AHPC, expressed only trace levels of Bax.

To determine whether Bak, which was highly expressed in H460 cells, played a role in Bcl-2-dependent apoptosis induced by TR3, the effects of Bak siRNA transfection was examined. Significant reductions of Bak protein were observed when H460 cells were transfected with Bak siRNA but not control siRNA, correlating with significant repression of TR3-dependent 3-Cl-AHPC-induced apoptosis. Thus, Bcl-2-dependent apoptosis induced by TR3 depends on multidomain pro-apoptotic Bcl-2-family proteins such as Bak.

VI. Methods for Screening Peptides, Analogs, and Small Molecules that Modulate Bcl-2-Family Member Protein Activity The assays described above are designed to identify compounds that interact with (e.g., bind to) Bcl-2, Bcl-$X_L$, and other members of the Bcl-2-family of proteins, and modify their ability to regulate apoptosis. This regulation may be by mimicking TR3, by inducing an equivalent conformation change, by enhancing the TR3 effect or by inhibiting the TR3 effect.

The compounds which may be screened include, but are not limited to peptides, fragments thereof, and other organic compounds (e.g., peptidomimetics) that bind to the Bcl-2-family member and either mimic the activity triggered by the natural regulatory ligand (e.g., TR3 and TCTP), enhance the activity triggered by the natural regulatory ligand or inhibit the activity triggered by the natural ligand; as well as peptides, antibodies or fragments thereof, and other organic compounds that mimic the binding domain of the Bcl-2-family member and bind to and "neutralize" natural ligand.

Such compounds may include, but are not limited to, peptides such as, for example, soluble peptides, including but not limited to members of random peptide libraries; (see, e.g., Lam et al. 1991 *Nature* 354:82-84; Houghten et al. 1991 *Nature* 354:84-86), and combinatorial chemistry-derived molecular libraries made of D- and/or L-configuration amino acids, phosphopeptides (including, but not limited to, members of random or partially degenerate, directed phosphopeptide libraries; see, e.g., Songyang et al. 1993 *Cell* 72:767-778), antibodies including, but not limited to, polyclonal, monoclonal, humanized, anti-idiotypic, chimeric or single chain antibodies, and FAb, F(ab')$_2$ and FAb expression library fragments, and epitope-binding fragments thereof, and small organic or inorganic molecules.

Computer modeling and searching technologies permit identification of compounds, or the improvement of already identified compounds that can modulate Bcl-2-family member activity. Having identified such a compound or composition, the active sites or regions are identified. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found. Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential Bcl-2-family member modulating compounds.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites of Bcl-2, Bcl-$X_L$, and related proteins will be apparent to those of skill in the art.

Examples of molecular modeling systems are the CHARMM and QUANTA programs (Polygen Corporation, Waltham, Mass.). CHARMM performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific-proteins, such as Rotivinen et al. 1988 *Acta Pharm Fennica* 97:159-166; McKinaly and Rossmann 1989 *Annu Rev Pharmacol Toxicol* 29:111-122; Perry and Davies OSAR: Quantitative Structure-Activity Relationships in Drug Design, pp. 189-193, Alan R. Liss, Inc. (1989); Lewis and Dean 1989 *Proc R Soc Lond* 236:125-140 and 141-162; and, with respect to a model receptor for nucleic acid components, Askew et al. 1989, *J Am Chem Soc* 111: 1082-1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario).

One could also screen libraries of known compounds, including natural products or synthetic chemicals, and biologically active materials, including proteins, for compounds which exhibit binding properties similar to those of TR3, such as lack of competition with Bcl-G, or enhanced binding in the presence of Bcl-G.

One could also screen libraries of known compounds, including natural products or synthetic chemicals, and biologically active materials, including proteins, for compounds which enhance the activity of or binding of TR3 to Bcl-2.

Once identified, these compounds can be subjected to assays such as those described in the examples to identify whether the compounds increase apoptosis or decrease apoptosis in cells.

Compounds identified via assays such as those described herein may be useful, for example, in inducing or inhibiting apoptosis.

VII. In Vitro Screening Assays for Compounds that Bind to Bcl-2-Family Member Proteins In vitro systems may be designed to identify compounds capable of interacting with (e.g., binding to) Bcl-2-family members. Compounds identified may be useful, for example, in modulating the activity of wild type and/or mutant Bcl related proteins; may be useful in elaborating the biological function of the Bcl related proteins; may be utilized in screens for identifying compounds that disrupt normal Bcl-2-family member interactions; or may in themselves disrupt such interactions.

The principle of the assays used to identify compounds that bind to the Bcl-2-family member involves preparing a reaction mixture of the protein and the test compound under conditions and for a time sufficient to allow the two components to interact and bind, thus forming a complex which can be removed and/or detected in the reaction mixture.

The screening assays can be conducted in a variety of ways. For example, one approach would involve anchoring the Bcl-2 related protein, polypeptide, peptide or fusion protein or the test substance to a solid phase, and detecting complexes of Bcl-2 related protein bound to test compounds anchored on the solid phase. In one embodiment, the Bcl-2 related reactant may be anchored to a solid surface and the test compound, which is not anchored, may be labeled, either directly or indirectly. Bound compound(s) could then be detected by various methods such as mass spectrometry after elution from the bound protein. In another embodiment, the binding specificity of test compounds can be tested using a competition assay as follows: a) Bcl-2 or Bcl-$X_L$ is anchored to a solid phase; b) immobilized Bcl-2 or Bcl-$X_L$ is incubated with TCTP or TR3 labeled with a fluorescent tag or other reporter molecule, in the presence or absence of compounds being tested; c) after incubation under suitable conditions, the solid phase is washed to remove unbound reactants; d) the amount of labeled TCTP or TR3 bound to the solid phase is measured for each reaction; and e) the amount of labeled TCTP or TR3 bound in the presence of various test compounds is compared with the amount of labeled TCTP or NR3 bound in the absence of test compounds, and the ability of each test compound to compete for Bcl-2 or Bcl-$X_L$ binding sites is determined.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected, e.g., using an immobilized antibody specific for the Bcl related protein, polypeptide, peptide or fusion protein or the test compound to anchor any complexes formed in solution, and a labeled antibody specific for the other component of the possible complex to detect anchored complexes.

Alternatively, cell-based assays can be used to identify compounds that interact with Bcl-2-family members. To this end, cell lines that express Bcl related proteins, or cell lines (e.g., COS cells, CHO cells, fibroblasts, etc.) that have been genetically engineered to express Bcl-2 related proteins (e.g., by transfection or transduction of DNA) can be used.

VIII. Assays for Intracellular Proteins that Interact with the Bcl-2-Family Members, TR3, and TCTP Any method suitable for detecting protein-protein interactions may be employed for identifying transmembrane proteins or intracellular proteins that interact with Bcl-2 or related proteins. Among the traditional methods which may be employed are co-immunoprecipitation, crosslinking and co-purification through gradients or chromatographic columns of cell lysates or proteins obtained from cell lysates or recombinantly produced to identify proteins in the lysate that interact with the Bcl related protein. For these assays, the Bcl related component used can be a full-length, a soluble derivative lacking the membrane-anchoring region, a peptide corresponding to a binding domain or a fusion protein containing the binding domain. Once isolated, such an intracellular protein can be identified and can, in turn, be used, in conjunction with standard techniques, to identify proteins with which it interacts. For example, at least a portion of the amino acid sequence of an intracellular protein which interacts with the Bcl related protein can be ascertained using techniques well known to those of skill in the art, such as via the Edman degradation technique. (See, e.g., Creighton, *Proteins: Structures and Molecular Principles*, W.H. Freeman & Co., N.Y. (1983) pp. 34-49). The amino acid sequence obtained may be used as a guide for the generation of oligonucleotide mixtures that can be used to screen for gene sequences encoding such intracellular proteins. Screening may be accomplished, for example, by standard hybridization or PCR techniques. Techniques for the generation of oligonucleotide mixtures and the screening are well-known. (See, e.g., Ausubel supra, and *PCR Protocols: A Guide to Methods and Applications*, Innis, M. et al., eds. Academic Press, Inc., New York, 1990).

Additionally, methods may be employed which result in the simultaneous identification of genes which encode proteins interacting with Bcl-2-family members. These methods include, for example, probing expression libraries in a manner similar to the well known technique of antibody probing of λgt11 libraries using labeled Bcl-2 related proteins, or a Bcl-2 related polypeptide, peptide or fusion protein. Protein-protein interactions can be measured using Fluorescence Resonance Energy Transfer (FRET), e.g., by labeling Bcl-2-family members and proteins that interact with Bcl-2-family members with suitable FRET probes such as, but not limited to, 5-(dimethylamino)naphthalene-1-sulfonyl chloride (dansyl chloride or DNS-CL) attached to Tyr-69 and N-[[4-[4-(dimethylamino)phenyl]azo]phenyl]maleimide (DABMI) or N-[4-(dimethylamino)-3,5-dinitrophenyl]maleimide (DDPM). Alternately, two-hybrid systems can be used either to confirm protein-protein interactions, or to search for previously unknown proteins capable of binding Bcl-2-family members.

The two-hybrid system for detecting protein-protein interactions in vivo is described in detail for illustration only and not by way of limitation. One version of this system has been described (Chien et al. 1991 *PNAS USA* 88:9578-9582) and is commercially available (Clontech, Palo Alto, Calif.). Briefly, plasmids are constructed that encode two hybrid proteins: one plasmid consists of nucleotides encoding the DNA-binding domain of a transcription activator protein fused to a nucleotide sequence encoding the Bcl-2-family member, a polypeptide, peptide or fusion protein, and the other plasmid consists of nucleotides encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast *Saccharomyces cerevisiae* that contains a reporter gene that expresses a protein (e.g., HBS or lacZ) whose regulatory region contains the binding site of the transcription activator. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, Bcl-2 may be used as the bait gene product. Total genomic or cDNA sequences are fused to the DNA encoding an activation domain. This library and a plasmid encoding a hybrid of a bait Bcl-2 gene product fused to the DNA-binding domain are cotransformed into a yeast reporter strain, and the resulting transformants are screened for those that express the reporter gene. For example, and not by way of limitation, a bait Bcl-2 gene sequence can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait Bcl-2 related gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait Bcl-2 gene-GAL4 fusion plasmid into a yeast strain which contains a lacZ gene driven by a promoter which contains GAL4 activation sequence. A cDNA encoded protein, fused to GAL4 transcriptional activation domain, that interacts with bait obR gene product will reconstitute an active GAL4 protein and thereby drive expression of the HIS3 gene. Colonies which express HIS3 can be detected by their growth on Petri dishes containing semi-solid agar based media lacking histidine. The cDNA can then be purified from these strains, and used to produce and isolate the bait Bcl-2 gene-interacting protein using techniques routinely practiced in the art.

Similarly, TR3 and TCTP could serve as targets in the above assays to find interacting proteins and related compounds.

IX. Structure-Based Drug Design

To aid in the characterization and optimization of compounds which can alter the activity of Bcl-2-family proteins, structure-based drug design has become a useful tool. Solution nuclear magnetic resonance (NMR) techniques can be used to map the interactions between the BH3 domain of the Bcl-2-family protein and chemical compounds that target these anti-apoptotic proteins. NMR chemical shift perturbation is an efficient tool for rapid mapping of interaction interfaces on proteins. Structure-activity relationships (SAR) can be obtained by using nuclear magnetic resonance (NMR), using the method known as "SAR by NMR" (Shuker et al. 1996 *Science* 274:1531; Lugovskoy et al. 2002 *J Am Chem Soc* 124:1234). SAR by NMR can be used to identify, optimize and link together small organic molecules that bind to proximal subsites of a protein to produce high-affinity ligands.

In using NMR to structurally characterize protein-protein and ligand-protein interactions, isotope labeling can result in increased sensitivity and resolution, and in reduced complexity of the NMR spectra. The three most commonly used stable isotopes for macromolecular NMR are $^{13}$C, $^{15}$N and $^{2}$H. Isotope labeling has enabled the efficient use of heteronuclear multi-dimensional NMR experiments, providing alternative approaches to the spectral assignment process and additional structural constraints from spin-spin coupling. Uniform isotope labeling of the protein enables the assignment process through sequential assignment with multidimensional triple-resonance experiments and supports the collection of conformational constraints in de novo protein structure determinations (Kay et al. 1990 *J Magn Reson* 89:496; Kay et al 1997 *Curr Opin Struct Biol* 7:722). These assignments can be used to map the interactions of a ligand by following chemical-shift changes upon ligand binding. In addition, intermolecular NOE (nuclear Overhauser effect) derived inter-molecular distances can be obtained to structurally characterize protein-ligand complexes.

In addition to uniform labeling, selective labeling of individual amino acids or labeling of only certain types of amino acids in proteins can result in a dramatic simplification of the spectrum and, in certain cases, enable the study of significantly larger macromolecules. For example, the methyl groups of certain amino acids can be specifically labeled with $^{13}$C and $^{1}$H in an otherwise fully $^{2}$H-labeled protein. This results in well resolved heteronuclear [$^{13}$C,$^{1}$H]-correlation spectra, which enables straightforward ligand-binding studies either by chemical shift mapping or by protein methyl-ligand inter-molecular NOEs, thus providing key information for structure-based drug design in proteins as large as 170 kDa (Pellecchia et al. 2002 *Nature Rev Drug Discovery* 1:211). 2D [$^{13}$C,$^{1}$H]-HMQC (heteronuclear multiple quantum coherence) and $^{13}$C-edited [$^{1}$H,$^{1}$H]-NOESY NMR experiments on a ligand-receptor complex can be used to detect binding, determine the dissociation constant for the complex, and provide a low-resolution model based on the available three-dimensional structure of the target, thus revealing the relative position of the ligand with respect to labeled side-chains.

Thus, NMR can be used to identify molecules that induce apoptosis. Compounds can be screened for binding to labeled Bcl-$X_L$, for example. Such labels include $^{15}$N and $^{13}$C. The interaction between the compound and Bcl-$X_L$, and therefore its ability to induce apoptosis, are determined via NMR.

X. Gene Therapy

Nucleic acid encoding TR3, TCTP, and deletions, truncations and variations thereof, as well as any other peptides identified by the methods above may be used in gene therapy. In gene therapy applications, genes are introduced into cells in order to achieve in vivo synthesis of a therapeutically effective product, for example the replacement of a defective gene. "Gene therapy" includes both conventional gene therapy where a lasting effect is achieved by a single treatment, and the administration of gene therapeutic agents, which involve the one time or repeated administration of a therapeutically effective DNA or mRNA. Antisense RNAs and DNAs can be used as therapeutic agents for blocking the expression of certain genes in vivo. It has been shown that short antisense oligonucleotides can be imported into cells where they act as inhibitors, despite their low intracellular concentrations caused by their restricted uptake by the cell membrane (Zamecnik et al. 1986 *PNAS USA* 83:4143-4146). The oligonucleotides can be modified, e.g., by substituting their negatively charged phosphodiester groups by uncharged groups.

There are a variety of techniques available for inducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include, but are not limited to, the use of liposomes, electroporation, microinjection, cell fusion, DEAE-dextran, and calcium phosphate precipitation method. The currently preferred in vivo gene transfer techniques include transfection with viral (typically retroviral) vectors and viral coat protein-liposome mediated transfection (Dzau et al. 1993 *Trends in Biotechnology* 11:205-210). In some situations it is desirable to provide the nucleic acid source with an agent that targets the target cell, such as an antibody specific for a cell surface membrane protein or the target cell, or a ligand for a receptor on the target cell. Where liposomes are employed, proteins which bind to a cell surface membrane protein associated with endocytosis may be used for targeting and/or to facilitate uptake, e.g., capsid proteins or fragments thereof that are tropic for a particular cell type, antibodies for proteins which undergo internalization in cycling, and proteins that target intracellular localizations and enhance intracellular half-life. The technique of receptor-mediated endocytosis is described, e.g., by Wu et al. 1987 *J Biol Chem* 262:4429-4432 and Wagner et al. 1990 *PNAS USA* 87:3410-3414. For review of gene therapy protocols see Anderson et al. 1992 *Science* 256:808-813.

Given the teachings set forth herein, the skilled artisan may select among various vectors and other expression/delivery elements depending on such factors as the site and route of administration and the desired level and duration of expression.

For example, naked plasmid DNA can be introduced into muscle cells, for example, by direct injection into the tissue (Wolff et al. 1989 *Science* 247:1465).

DNA-Lipid Complexes—Lipid carriers can be associated with naked DNA (e.g., plasmid DNA) to facilitate passage through cellular membranes. Cationic, anionic, or neutral lipids can be used for this purpose. However, cationic lipids are preferred because they have been shown to associate better with DNA which, generally, has a negative charge. Cationic lipids have also been shown to mediate intracellular delivery of plasmid DNA (Felgner and Ringold 1989 *Nature* 337:387). Intravenous injection of cationic lipid-plasmid complexes into mice has been shown to result in expression of the DNA in lung (Brigham et al. 1989 *Am J Med Sci* 298:278). See also, Osaka et al. 1996 *J Pharm Sci* 85:612-618; San et al. 1993 *Human Gene Therapy* 4:781-788; Senior et al. 1991 *Biochim Biophys Acta* 1070:173-179; Kabanov and Kabanov 1995 *Bioconjugate Chem* 6:7-20; Remy et al. 1994 *Bioconjugate Chem* 5:647-654; Behr 1994 *Bioconjugate Chem* 5:382-389; Behr et al. 1989 *PNAS USA* 86:6982-6986; and Wyman et al. 1977 *Biochem* 36:3008-3017.

Adenovirus-based vectors for the delivery of transgenes are well known in the art and may be obtained commercially or constructed by standard molecular biological methods. Recombinant adenoviral vectors containing exogenous genes for transfer are, generally, derived from adenovirus type 2 (Ad2) and adenovirus type 5 (Ad5). They may also be derived from other non-oncogenic serotypes. See, e.g., Horowitz, "*Adenoviridae and their Replication*" in *Virology*, 2d Ed., Fields et al. eds., Raven Press Ltd., New York (1990) incorporated herein by reference.

It has been shown that TR3 and TCTP specifically interact with Bcl-2-family receptors, resulting in the conversion of these molecules from anti-apoptotic to pro-apoptotic. These studies provide a molecular basis for developing various anticancer drugs and other therapeutic agents.

XI. Methods of Identifying Antibodies which Induce a Conformational Change in Bcl-2 Comparable to that Induced by TR3

Antibodies against the loop domain of Bcl-2. The N-terminal loop region of Bcl-2 can be expressed and used as an antigen to develop anti-Bcl-2/N-terminal loop region antibodies. These antibodies, by binding to the loop domain of Bcl-2 can mimic the activity of TR3 in the induction of a conformational change of Bcl-2 which will expose the hidden BH3 domain and confer pro-apoptotic activity to the Bcl-2 protein. To identify antibodies that bind to the loop region, an ELISA assay can be used which is set up with various anti-loop antibodies for capture and an anti-BH2 antibody for detection.

Assays to determine whether the antibody can mimic TR3 can be set up in a cellular system by transfecting the antibodies into TR3-expression Bcl-2 deleted cells and looking for cellular effects.

These antibodies may be used to treat cancers or any diseases of decreased apoptosis or over-proliferation of cells. These antibodies may also be used to identify other therapeutic molecules which induce an equivalent conformational change to TR3. For example, compounds which inhibit the interaction between the antibody and Bcl-2 may be identified. Bcl-2 can be contacted with a candidate compound and a BH3-specific antibody (or any antibody which mimics TR3 by inducing a conformational change in Bcl-2). The contact may occur under conditions where the BH3 domain of Bcl-2 is not accessible to a BH3 specific antibody. The association of the BH3 specific antibody to the BH3 domain of Bcl-2 is then detected, whereby the candidate compound is identified as an agent that induces apoptosis or an agent that interferes with binding of the BH3 specific antibody or an agent that allows the interaction between Bcl-2 and the anti-BH3 specific antibody. Thus, the assay may be set up to identify a compound that interferes with the binding of the antibody, or a compound that induces a conformational change allowing the antibody to bind.

Further, Bcl-$X_L$ antibodies which mimic the activity of TCTP may be identified in the same way and used for therapeutics.

XII. Methods of Diagnosis Using Antibodies which Recognize the Conformational Change in Bcl-2 which is Induced by TR3

Antibodies described herein that are capable of binding to the conformationally changed Bcl-2 (for example to the conformationally accessible BH3 domain) can be used to identify the presence or absence or amount of the Bcl-2 which is conformationally changed in patient samples (the Bcl-2 epitope) and can be useful as diagnostics as described hereinbelow in addition to their therapeutic effectiveness in the treatment of malignant tissue growth and/or disease, such as cancer and obstructive tissue growths. In its simplest embodiment, such an antibody may be able to recognize the BH3 domain which is exposed by TR3 binding.

An Enzyme-Linked Immunosorbent Assay (ELISA) for the detection of the epitope of Bcl-2 in a sample can be developed. In the assay, wells of a microtiter plate, such as a 96-well microtiter plate or a 384-well microtiter plate, are adsorbed for several hours with a first fully human (for example) monoclonal antibody directed against the epitope. The immobilized antibody serves as a capture antibody for any of the antigen that can be present in a test sample. The wells are rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample can be, for example, a serum sample from a subject suspected of having levels of circulating antigen considered to be diagnostic of a pathology, for example, a cancer.

After rinsing away the test sample or standard, the wells are treated with a second fully human monoclonal anti-Bcl-2 antibody that is labeled by conjugation with biotin. The labeled anti-Bcl-2 antibody serves as a detecting antibody. After rinsing away excess second antibody, the wells are treated with avidin-conjugated horseradish peroxidase (HRP) and a suitable chromogenic substrate. The concentration of the antigen in the test samples is determined by comparison with a standard curve developed from the standard samples.

This ELISA assay provides a highly specific and very sensitive assay for the detection of the Bcl-2 epitope (which mimics the conformation change induced by TR3) in a test sample.

For determination of the epitope of Bcl-2 in patients, a sandwich ELISA is developed which works with human serum and/or tissue samples from the patient. The two fully human monoclonal anti-bcl-2 antibodies used in the sandwich ELISA, recognizes different epitopes on the bcl-2 molecule. Normal or patient sera can be diluted in blocking buffer. This method can be used for diagnosing the presence of a cancer or staging of cancer in a patient based on the amount of the conformationally induced Bcl-2 present.

To develop the assay for a given type of cancer, samples of blood are taken from subjects diagnosed as being at various stages in the progression of the disease, and/or at various points in the therapeutic treatment of the cancer. The concentration of the specific Bcl-2 epitope or antigen present in the blood samples is determined using a method that specifically determines the amount of the antigen that is present. Such a method includes an ELISA method. This may also be used to stage the progression of the cancer in a subject under study, or to characterize the response of the subject to a course of therapy.

Further antibodies which recognize the conformationally changed Bcl-$X_L$ can be used for diagnosis and prognosis in the same way as those for Bcl-2 above.

What is claimed is:

1. A method of inducing apoptosis in a cell, comprising contacting said cell with a peptide compound capable of inducing a conformational change in Bcl-2, so as to convert said Bcl-2 into a pro-apoptotic form, without cleaving said Bcl-2 wherein said compound comprises a BCL-2 binding fragment of the human TR3 receptor of SEQ ID NO: 3.

2. The method of claim 1, wherein said fragment comprises the 69 amino acids between amino acids 467 and 536 of the human TR3 receptor of SEQ ID NO: 3.

3. The method of claim 1, wherein the compound comprises at least one D-amino acid.

4. The method of claim 1, wherein said compound binds to the N-terminal portion of Bcl-2.

5. The method of claim 4, wherein said compound binds to amino acids 1-80 of the N terminal portion of Bcl-2.

* * * * *

UNITED STATES PATENT AND TRADEMARK OFFICE
CERTIFICATE OF CORRECTION

PATENT NO. : 7,491,700 B2
APPLICATION NO. : 11/619965
DATED : February 17, 2009
INVENTOR(S) : Reed et al.

It is certified that error appears in the above-identified patent and that said Letters Patent is hereby corrected as shown below:

Title Page Item (56)

(OTHER PUBLICATIONS)

Page 1, Line 17, delete "steriod" and replace it with --steroid--.

Page 1, Line 10, delete "myloid" and replace it with --myeloid--.

Page 1, Line 38, delete "Maliganancis" and replace it with --Malignancies--.

Page 1, Line 50, delete "Denocarcinoma" and replace it with --adenocarcinoma--.

Specification

Col. 2, Line 40-41, delete "Sinbis" and replace it with --Sindbis--.

Col. 7, Line 33, delete "$CH_2CH_2$—" and replace it with -- —$CH_2CH_2$— --.

Col. 10, Line 27-28, delete "benzyloxycarboyl" and replace it with --benzyloxycarbonyl--.

Col. 10, Line 48, delete "mesitoylsulfonyl" and replace it with --mesitylsulfonyl--.

Col. 11, Line 33 (Approx.), delete "hetereocyclic." and replace it with --heterocyclic.--.

Col. 14, Line 62-63, delete "diimadozle" and replace it with --diimidazole--.

Col. 14, Line 64-65, delete "diazoiumbenzyl" and replace it with --diazoniumbenzyl--.

Col. 16, Line 1, delete "NR" and replace it with --$NR^6$--.

Col. 20, Line 27, delete "A" and replace it with --Δ--.

Col. 21, Line 64, delete "Amexa" and replace it with --Amaxa--.

Col. 21, Line 65, delete "Nucleofectorm" and replace it with --Nucleofector™--.

Col. 25, Line 48, delete "A" and replace it with --Δ--.

UNITED STATES PATENT AND TRADEMARK OFFICE
CERTIFICATE OF CORRECTION

PATENT NO. : 7,491,700 B2
APPLICATION NO. : 11/619965
DATED : February 17, 2009
INVENTOR(S) : Reed et al.

It is certified that error appears in the above-identified patent and that said Letters Patent is hereby corrected as shown below:

Col. 25, Line 67, delete "TR3/(DBD (TR3/(DBD/(DC1)" and replace it with --TR3/$\Delta$DBD (TR3/$\Delta$DBD/$\Delta$DC1)--.

Col. 26, Line 8, delete "A" and replace it with --$\Delta$--.

Col. 26, Line 9, delete "A" and replace it with --$\Delta$--.

Col. 26, Line 11, delete "1483" and replace it with --I483--.

Col. 28, Line 26, before "471" delete "A" and replace it with --$\Delta$--.

Col. 28, Line 33, delete "A" and replace it with --$\Delta$--.

Col. 28, Line 39, delete "(NJK)" and replace it with --(JNK)--.

Col. 28, Line 40, delete "(" and replace it with --$\Delta$--.

Col. 28, Line 42, before "471" delete "(" and replace it with --$\Delta$--.

Col. 28, Line 51, delete "A" and replace it with --$\Delta$--.

Col. 29, Line 42, delete "(" and replace it with --$\Delta$--

Col. 29, Line 44, delete "(" and replace it with --$\Delta$--.

Col. 30, Line 6, before "DBD" delete "(" and replace it with --$\Delta$--.

Col. 30, Line 44, delete "(" and replace it with --/$\Delta$--.

Col. 31, Line 53, delete "A" and replace it with --$\Delta$--.

Col. 31, Line 54, delete "1483" and replace it with --I483--.

Col. 32, Line 55, delete "Tarpeting" and replace it with --Targeting--.

UNITED STATES PATENT AND TRADEMARK OFFICE
CERTIFICATE OF CORRECTION

PATENT NO. : 7,491,700 B2
APPLICATION NO. : 11/619965
DATED : February 17, 2009
INVENTOR(S) : Reed et al.

It is certified that error appears in the above-identified patent and that said Letters Patent is hereby corrected as shown below:

Col. 35, Line 23, delete "B3" and replace it with --BH3--.

Col. 39, Line 53, delete "DNS-CL" and replace it with --DNS-C1--.

Signed and Sealed this

First Day of September, 2009

David J. Kappos
*Director of the United States Patent and Trademark Office*

SEQUENCE LISTING

<160> NUMBER OF SEQ ID NOS: 3

<210> SEQ ID NO 1
<211> LENGTH: 18
<212> TYPE: PRT
<213> ORGANISM: Homo sapiens

<400> SEQUENCE: 1

His Arg Leu Gly Cys Ala Arg Gly Phe Gly Asp Trp Ile Asp Ser Ile
1               5                   10                  15

Leu Ala

<210> SEQ ID NO 2
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 2
caguccagcc augcuccu                                                           18

<210> SEQ ID NO 3
<211> LENGTH: 598
<212> TYPE: PRT
<213> ORGANISM: Homo sapiens

<400> SEQUENCE: 3

Met Pro Cys Ile Gln Ala Gln Tyr Gly Thr Pro Ala Pro Ser Pro Gly
1               5                   10                  15

Pro Arg Asp His Leu Ala Ser Asp Pro Leu Thr Pro Glu Phe Ile Lys
                20                  25                  30

Pro Thr Met Asp Leu Ala Ser Pro Glu Ala Ala Pro Ala Ala Pro Thr
        35                  40                  45

Ala Leu Pro Ser Phe Ser Thr Phe Met Asp Gly Tyr Thr Gly Glu Phe
    50                  55                  60

Asp Thr Phe Leu Tyr Gln Leu Pro Gly Thr Val Gln Pro Cys Ser Ser
65                  70                  75                  80

Ala Ser Ser Ser Ala Ser Ser Thr Ser Ser Ser Ala Thr Ser Pro
                85                  90                  95

Ala Ser Ala Ser Phe Lys Phe Glu Asp Phe Gln Val Tyr Gly Cys Tyr
                100                 105                 110

Pro Gly Pro Leu Ser Gly Pro Val Asp Glu Ala Leu Ser Ser Ser Gly
            115                 120                 125

Ser Asp Tyr Tyr Gly Ser Pro Cys Ser Ala Pro Ser Pro Ser Thr Pro
    130                 135                 140

Ser Phe Gln Pro Pro Gln Leu Ser Pro Trp Asp Gly Ser Phe Gly His
145                 150                 155                 160

Phe Ser Pro Ser Gln Thr Tyr Glu Gly Leu Arg Ala Trp Thr Glu Gln
                165                 170                 175

Leu Pro Lys Ala Ser Gly Pro Pro Gln Pro Pro Ala Phe Phe Ser Phe
            180                 185                 190

Ser Pro Pro Thr Gly Pro Ser Pro Ser Leu Ala Gln Ser Pro Leu Lys
        195                 200                 205

Leu Phe Pro Ser Gln Ala Thr His Gln Leu Gly Glu Gly Glu Ser Tyr
    210                 215                 220

-continued

```
Ser Met Pro Thr Ala Phe Pro Gly Leu Ala Pro Thr Ser Pro His Leu
225                 230                 235                 240

Glu Gly Ser Gly Ile Leu Asp Thr Pro Val Thr Ser Thr Lys Ala Arg
                245                 250                 255

Ser Gly Ala Pro Gly Gly Ser Glu Gly Arg Cys Ala Val Cys Gly Asp
            260                 265                 270

Asn Ala Ser Cys Gln His Tyr Gly Val Arg Thr Cys Glu Gly Cys Lys
        275                 280                 285

Gly Phe Phe Lys Arg Thr Val Gln Lys Asn Ala Lys Tyr Ile Cys Leu
    290                 295                 300

Ala Asn Lys Asp Cys Pro Val Asp Lys Arg Arg Arg Asn Arg Cys Gln
305                 310                 315                 320

Phe Cys Arg Phe Gln Lys Cys Leu Ala Val Gly Met Val Lys Glu Val
                325                 330                 335

Val Arg Thr Asp Ser Leu Lys Gly Arg Arg Gly Arg Leu Pro Ser Lys
            340                 345                 350

Pro Lys Gln Pro Pro Asp Ala Ser Pro Ala Asn Leu Leu Thr Ser Leu
        355                 360                 365

Val Arg Ala His Leu Asp Ser Gly Pro Ser Thr Ala Lys Leu Asp Tyr
    370                 375                 380

Ser Lys Phe Gln Glu Leu Val Leu Pro His Phe Gly Lys Glu Asp Ala
385                 390                 395                 400

Gly Asp Val Gln Gln Phe Tyr Asp Leu Leu Ser Gly Ser Leu Glu Val
                405                 410                 415

Ile Arg Lys Trp Ala Glu Lys Ile Pro Gly Phe Ala Glu Leu Ser Pro
            420                 425                 430

Ala Asp Gln Asp Leu Leu Leu Glu Ser Ala Phe Leu Glu Leu Phe Ile
        435                 440                 445

Leu Arg Leu Ala Tyr Arg Ser Lys Pro Gly Glu Gly Lys Leu Ile Phe
    450                 455                 460

Cys Ser Gly Leu Val Leu His Arg Leu Gln Cys Ala Arg Gly Phe Gly
465                 470                 475                 480

Asp Trp Ile Asp Ser Ile Leu Ala Phe Ser Arg Ser Leu His Ser Leu
                485                 490                 495

Leu Val Asp Val Pro Ala Phe Ala Cys Leu Ser Ala Leu Val Leu Ile
            500                 505                 510

Thr Asp Arg His Gly Leu Gln Glu Pro Arg Arg Val Glu Glu Leu Gln
        515                 520                 525

Asn Arg Ile Ala Ser Cys Leu Lys Glu His Val Ala Ala Val Ala Gly
    530                 535                 540

Glu Pro Gln Pro Ala Ser Cys Leu Ser Arg Leu Leu Gly Lys Leu Pro
545                 550                 555                 560

Glu Leu Arg Thr Leu Cys Thr Gln Gly Leu Gln Arg Ile Phe Tyr Leu
                565                 570                 575

Lys Leu Glu Asp Leu Val Pro Pro Pro Ile Ile Asp Lys Ile Phe
            580                 585                 590

Met Asp Thr Leu Pro Phe
            595
```